(12) United States Patent
Kornberg et al.

(10) Patent No.: US 6,455,698 B1
(45) Date of Patent: Sep. 24, 2002

(54) CONFORMATIONALLY SEMI-CONSTRAINED QUINOXALINE 2,3-DIONES AS NEUROPROTECTIVE AGENTS

(75) Inventors: Brian Edward Kornberg; Sham Shridhar Nikam; Michael Francis Rafferty, all of Ann Arbor, MI (US)

(73) Assignee: Warner-Lambert Company, Morris Plains, NJ (US)

(*) Notice: Subject to any disclaimer, the term of this patent is extended or adjusted under 35 U.S.C. 154(b) by 0 days.

(21) Appl. No.: 09/971,237

(22) Filed: Oct. 4, 2001

Related U.S. Application Data

(60) Division of application No. 09/199,627, filed on Nov. 25, 1998, now Pat. No. 6,340,758, which is a continuation-in-part of application No. 09/025,295, filed on Feb. 13, 1998, now abandoned.
(60) Provisional application No. 60/046,626, filed on May 16, 1997.

(51) Int. Cl.$^7$ ............................................. C07D 241/28

(52) U.S. Cl. ........................................ 544/354; 544/353

(58) Field of Search ................................. 544/354, 353

(56) References Cited

U.S. PATENT DOCUMENTS

| | | | |
|---|---|---|---|
| 5,783,572 A | * | 7/1998 | Mowbray et al. ............ 544/354 |
| 5,874,426 A | * | 2/1999 | Kornberg .................... 544/343 |

FOREIGN PATENT DOCUMENTS

| | | | |
|---|---|---|---|
| EP | 0488959 | | 6/1992 |
| JP | 06228112 | * | 2/1993 |
| WO | 97/32873 | * | 9/1987 |
| WO | 9708155 | | 3/1997 |

OTHER PUBLICATIONS

C.F. Bigge, and T.C. Malone, "Agonists, Antagonists and Modulators of the N–methyl–D–aspartic acid (NMDA) and г–amino–3–hydroxy–5–methyl–4–isoxazolepropanole acid (AMPA) Subtypes of Glutamate Receptors", *Current Opinion in Therapeutic Patents*, 1993, pp 951–989.

M. Rogawski, "Therapeutic potential of excitatory amino acid antagonists: channel blockers and 2,3–benzodiazepines", *TiPS*, vol. 14, 1993, pp 325–331.

H. Li and A.M. Buchan, "Treatment with an AMPA, Antagonist 12 Hours Following Severe Normothermic Forebrain Ischemia Prevents CA$_1$ Neuronal Injury", *Journal of Cerebral Blood Flow and Metabolism*, vol. 13, No. 6, 1993, pp 933–939.

B. Nellgård and T. Wieloch, "Postischemic Blockade of AMPA but not NMDA Receptors Mitigates Neuronal Damage in the Rat Brain Following Transient Severe Cerebral Ischemia", *Journal of Cerebral Blood Flow and Metabolism*, vol. 12, No. 1, 1992, pp 2–11.

R. Bullock et al., "Neuroprotective Effect of the AMPA Receptor Antagonist LY–293558 in Focal Cerebral Ischemia", *Journal of Cerebral Blood Flow and Metabolism*, vol. 14, No. 3, 1994, pp 466–471.

D. Xue et al., "Delayed Treatment with AMPA, but Not NMDA, Antagonists Reduces Neocortical Infarction", *Journal of Cerebral Blood Flow and Metabolism*, vol. 14, No. 2, 1994, pp 251–261.

X.–J. Xu et al., "Systemic Excitatory Amino Acid Receptor Antagonists of the г–amino–3–hydroxy–5–methyl–4–isoxazolepropionic acid (AMPA) Receptor and of the N–methyl–D–aspartatic (NMDA) Receptor Relieve Mechanical Hypersensitivity After Transient Spinal Cord Ischemis in Rats", *The Journal of Pharmacology and Experimental Therapeutics*, vol. 267, No. 1, 1993, pp 140–144.

T. Namba et al., "Antiepileptic and anticonvulsant effects of NBQX, a selective AMPA receptor antagonist, in the rat kindling model of epilepsy", *Brain Research*, vol. 638, 1994, pp 36–44.

S.E. Brown and J. McCulloch, "AMPA receptor antagonists and local cerebral glucose utilization in the rat", *Brain Research*, vol. 641, 1994, pp 10–20.

S. Smith et al., "The non–N–methyl–D–aspartate receptor Antagonists, BYKI 52466 and NBQX are anticonvulsant in two animal models of reflex epilepsy", *European Journal of Pharmacology*, vol. 201, 1991. pp. 179–183.

(List continued on next page.)

*Primary Examiner*—Mukund J. Shah
*Assistant Examiner*—Venkataraman Balasubramanian
(74) *Attorney, Agent, or Firm*—Elizabeth M. Anderson; Charles W. Ashbrook; David R. Kurlandsky

(57) ABSTRACT

A process is disclosed for the preparation of a compound of formula

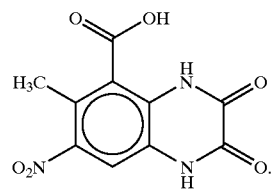

A process is also disclosed for preparing a compound of formula

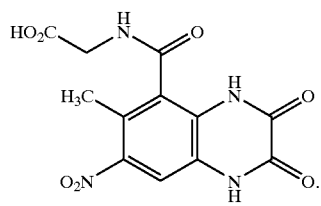

2 Claims, No Drawings

OTHER PUBLICATIONS

T. Klockgether and L. Turski, "Toward an Understanding of the Role of Glutamate in Experimental Parkinsonism: Agonist–Sensitive Sites in the Basal Ganglia", *Annals of Neurology*, vol. 34, No. 4, 1993, pp. 585–593.

T. Klockgether et al., "The AMPA Receptor Antagonist NMQX Has Antiparkinsonian Effects in Monamine–depleted Rats and MPTP–treated Monkeys", *Annals of Neurology*, vol. 30, No. 5, 1991, pp. 717–723.

P. Francis et al., "Conical Pyramidal Neurone Loss May Cause Glutamatergic Hypoacitivity and Cognitive Impairment in Alzheimer's Disease: Investigative and Therapeutic Perspectives", *Journal of Neurochemistry*, vol. 60, No. 5, 1993, pp. 1589–1604.

S. Lipton, "Prospects for clinically tolerated NMDA antagonists: open–channel blockers and alternative redox states of nitric oxide", *TINS*, vol. 16, No. 12, 1993, pp. 527–532.

S. Lipton and P. Rosenberg, "Excitatory Amino Acids as a Final Common Pathway for Neurologic Disorders", Review Article in *Mechanisms of Disease*, F. Epstein, Editor, vol. 380, No. 9, 1993, pp. 613–622.

C. Bigge, "Structural Requirements for the Development of Potent N–methyl–D–aspartic Acid (NMDA) Receptor Antagonists", *Biochemical Pharmacology*, vol. 45, No. 8, 1993, pp. 1547–1561.

Y. Auberson et al., "5–Aminomethylquinoxaline–2,3–diones. Part II: N–Aryl Derivatives As Novel NMDA/Glycine and AMPA Antagonists", *Bioorganic & Medicinal Chemistry Letters*, No. 8, 1998, pp. 71–74.

P. Acklin et al., "5–Aminomethylquinoxaline–2,3–diones, Part III: Arylamide Derivatives As Highly Potent and Selective Glycine–Site NMDA Receptor Antagonists", *Bioorganic & Medicinal Chemistry Letters*, No. 8, 1998, pp. 493–498.

S. Yamaguchi et al., "Anticonvulsant activity of AMPA/kainate antagonists: comparison of GYKI 52466 and NBQX in maximal electroshock and chemoconvulsant seizure models", *Epilepsy Research*, vol. 15, 1993, pp. 179–184.

\* cited by examiner

CONFORMATIONALLY SEMI-CONSTRAINED QUINOXALINE 2,3-DIONES AS NEUROPROTECTIVE AGENTS

CROSS REFERENCE TO RELATED APPLICATIONS

This application is a divisional of U.S. Ser. No. 09/199,627 filed Nov. 25, 1998, now U.S. Pat. No. 6,360,758, which is a continuation-in-part of U.S. Ser. No. 09/025,295 filed Feb. 13, 1998, now abandoned, having benefit of 60/046,626 filed May 16, 1997.

BACKGROUND OF THE INVENTION

The present invention concerns conformationally semi-constrained analogs of substituted quinoxaline 2,3-diones having utility as glutamate receptor antagonists. The quinoxaline 2,3-dione system is substituted by an amino acid derivative or nitrogen heterocyclic ring which includes bioisosteres of carboxylic acid derivatives via a carbon atom linkage. The compounds are active as excitatory amino acid receptor antagonists acting at glutamate receptors, including either or both N-methyl-D-aspartate (NMDA) receptors and non-NMDA receptors such as the I-amino-3-hydroxy-5-methyl-4-isoxazole propionic acid (AMPA) receptor and the kainate receptor. The invention also relates, therefore, to the use of those quinoxaline-2,3-diones as neuroprotective agents for treating conditions such as cerebral ischemia or cerebral infarction resulting from a range of phenomena, such as thromboembolic or hemorrhagic stroke, cerebral vasospasms, hypoglycemia, cardiac arrest, status epilepticus, perinatal asphyxia, anoxia such as from drowning, pulmonary surgery, and cerebral trauma, as well as to treat chronic neurodegenerative disorders such as Alzheimer's Disease, Parkinsonism, and Huntington's Disease, and seizure disorders and pain. The compounds of the present invention may also be useful in the treatment of schizophrenia, epilepsy, anxiety, pain, and drug addiction.

Excessive excitation by neurotransmitters can cause the degeneration and death of neurons. It is believed that this degeneration is in part mediated by the excitotoxic actions of the excitatory amino acids (EAA) glutamate and aspartate at the N-methyl-D-aspartate (NMDA) receptor, the I-amino-3-hydroxy-5-methyl-4-isoxazole propionic acid (AMPA) receptor, and the kainate receptor. AMPA/kainate receptors may be referred to jointly as non-NMDA receptors. This excitotoxic action is considered responsible for the loss of neurons in cerebrovascular disorders such as cerebral ischemia or cerebral infarction resulting from a range of conditions, such as thromboembolic or hemorrhagic stroke, cerebral vasospasm, hypoglycemia, cardiac arrest, status epilepticus, perinatal asphyxia, anoxia such as from drowning, pulmonary surgery, and cerebral trauma, as well as lathyrism, Alzheimer's Disease, Parkinson's Disease, and Huntington's Disease.

Several classes of quinoxalinedione derivatives have been disclosed as glutamate (EAA) receptor antagonists. For example, among excitatory amino acid receptor antagonists recognized for usefulness in the treatment of disorders are those that block AMPA receptors (Bigge C. F. and Malone T. C., *Curr. Opin. Ther. Pat.*, 1993:951; Rogawski M. A., *TiPS*, 1993;14:325). AMPA receptor antagonists have prevented neuronal injury in several models of global cerebral ischemia (Li H. and Buchan A. M., *J. Cerebr. Blood Flow Metab.*, 1993;13:933; Nellgard B. and Wieloch T., *J. Cerebr. Blood Flow Metab.*, 1992;12:2) and focal cerebral ischemia (Bullock R., Graham D. I., Swanson S., and McCulloch J., *J. Cerebr. Blood Flow Metab.*, 1994;14:466; Xue D., Huang Z. -G., Barnes K., Lesiuk H. J., Smith K. E., and Buchan A. M., *J. Cerebr. Blood Flow Metab.*, 1994;14:251). AMPA antagonists have also shown efficacy in models for analgesia (Xu X. -J., Hao J. -X, Seiger A., and Wiesenfeld-Hallin Z., *J. Pharmacol. Exp. Ther.*, 1993;267:140), and epilepsy (Namba T., Morimoto K., Sato K., Yamada N., and Kuroda S., *Brain Res.*, 1994;638:36; Brown S. E. and McCulloch J., *Brain Res.*, 1994;641:10; Yamaguchi S. I., Donevan S. D., and Rogawski M. A., *Epilepsy Res.*, 1993;15:179; Smith S. E., Durmuller N., and Meldrum B. S., *Eur. J. Pharmacol.*, 1991;201:179). AMPA receptor antagonists have also demonstrated promise in chronic neurodegenerative disorders such as Parkinsonism (Klockgether T., Turski L., Honoré T., Zhang Z., Gash D. M., Kurlan R., and Greenamyre J. T., *Ann. Neurol.*, 1993;34(4):585–593).

Excitatory amino acid receptor antagonists that block NMDA receptors are also recognized for usefulness in the treatment of disorders. NMDA receptors are intimately involved in the phenomenon of excitotoxicity, which may be a critical determinant of outcome of several neurological disorders. Disorders known to be responsive to blockade of the NMDA receptor include acute cerebral ischemia (stroke or cerebral trauma, for example), muscular spasm, convulsive disorders, neuropathic pain, and anxiety, and may be a significant causal factor in chronic neurodegenerative disorders such as Parkinson's Disease (Klockgether T. and Turski L., *Ann. Neurol.*, 1993;34:585–593), human immunodeficiency virus (HIV) related neuronal injury, amyotrophic lateral sclerosis (ALS), Alzheimer's Disease (Francis P. T., Sims N. R., Procter A. W., and Bowen D. M., *J. Neurochem.*, 1993;60(5):1589–1604), and Huntington's Disease. (See Lipton S., *TINS*, 1993;16(12):527–532; Lipton S. A. and Rosenberg P. A., *New Eng. J. Med.*, 1994;330 (9):613–622; and Bigge C. F., *Biochem. Pharmacol.*, 1993;45:1547–1561 and references cited therein.) NMDA receptor antagonists may also be used to prevent tolerance to opiate analgesia or to help control withdrawal symptoms from addictive drugs (European Patent Application 488, 959A).

The compounds of the instant invention differ from the art in that they provide non-coplanar compounds with greater solubility and, therefore, better ability to penetrate the blood-brain barrier. These are important attributes in pharmaceuticals. It is a further object to cover conformationally semi-constrained quinoxaline-2,3-dione derivatives.

SUMMARY OF THE INVENTION

Described are quinoxaline-dione compounds of Formula I

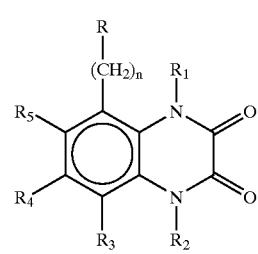

wherein

R is an amino acid, a derivative thereof, or nitrogen heterocyclic ring which is saturated or unsaturated of from 5 to 8 members which may have additional oxygen or sulfur atoms therein and which may be substituted by one or more substituents selected from:
alkyl of from 1 to 4 carbon atoms,
hydroxyl,
alkoxy of from 1 to 4 carbon atoms,
—$CF_3$,
—CN,
-amino,
—$C(O)R_{11}$, or
—$(CH_2)_n$-aryl of from 6 to 12 carbon atoms;
R must be attached through a carbon to the quinoxalinyl ring;
$R_1$ is H, alkyl of from 1 to 4 carbon atoms, phosphonoalkyl of from 1 to 4 carbon atoms, phosphoroalkyl of from 1 to 4 carbon atoms, carboxyalkyl of from 1 to 4 carbon atoms, —$(CH_2)_mC(O)R_{11}$, or hydroxy;
$R_2$ is hydrogen, hydroxy, or amine;
$R_3$ and R4 are each independently H, alkyl of from 1 to 4 carbon atoms, cycloalkyl of from 5 to 7 carbon atoms, alkenyl of from 2 to 6 carbon atoms, halogen, haloalkyl of from 1–6 carbon atoms, nitro, cyano, $SO_2CF_3$, $CH_2SO_2R_7$, $(CH_2)_mCO_2R_7$, $(CH_2)_mCONR_7R_8$, $(CH_2)_mSO_2NR_8R_9$, or $NHCOR_7$;
$R_5$ is H, alkyl of from 1 to 4 carbon atoms, alkenyl of from 2 to 6 carbon atoms, cycloalkyl of from 5 to 7 carbon atoms, halogen, haloalkyl of from 1 to 4 carbon atoms, —$(CH_2)_m$aryl of from 6 to 10 carbon atoms, nitro, cyano, $SO_2CF_3$, $(CH_2)_mCO_2R_9$, $(CH_2)_m CONR_9R_{10}$, $SO_2NR_9R_{10}$, $SO_2R_7$, $(CH_2)_m SO_2R_7$, $NHCOR_9$, —$(CH_2)_m$heterocyclic of from 6 to 10 atoms which may contain nitrogen, oxygen, sulfur, and/or —$(CH_2)_nR$,
$R_5$ may be joined at $R_4$ to form a cyclic aromatic or a heterocyclic ring of from 5 to 7 members which may contain nitrogen, oxygen, or sulfur; $R_7$, $R_8$, $R_9$, and $R_{10}$ are each independently selected from hydrogen, alkyl of from 1 to 4 carbon atoms, cycloalkyl of from 5 to 7 carbon atoms, haloalkyl of from 1 to 4 carbon atoms, or —$(CH_2)_mR_{11}$;
$R_{11}$ is alkyl or alkoxy of from 1 to 4 carbon atoms, hydroxy, or amino;
m is an integer of from 0 to 4;
n is an integer of from 0 to 4;
or a pharmaceutically acceptable salt thereof. Preferred compounds are those of Formula I wherein
R is an amino acid attached via an alkyl side-chain to the quinoxaline-2,3-dione ring at C-5 or C-6. The amino acid is R or S or RS(±). The point of attachment is I- to the carboxylic acid moiety, e.g.,

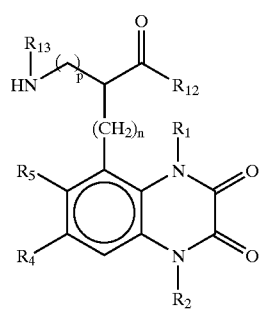

wherein
p is an integer of from 0 to 4;
$R_{12}$ is —OH, alkoxy, or —$NR_7R_8$;
$R_{13}$ is H, OH, $C(O)CH_3$, protecting groups such as alkyl, aralkyl, or aryl, Boc, CBZ, FMOC;

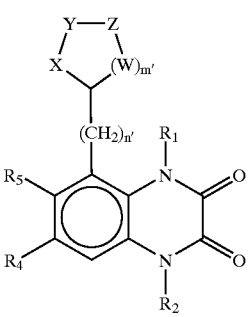

wherein
m' is an integer of from 1 to 3;
X, Y, Z, and W are each independently S, O, N, or C.

Or R is a nitrogen heterocyclic ring of 5 to 7 members with additional oxygen or sulfur atoms therein, and which includes bioisosteres of carboxylic acid, ester or amide, attached to the 5- or 6-quinoxalinyl side-chain via a carbon in the ring.

Some of the preferred compounds of the invention are selected from:

[(2,3-Dimethoxy-6-methyl-7-nitro-quinoxaline-5-carbonyl)-amino] acetic acid tert-butyl ester;

[(2,3-Dimethoxy-6-methyl-7-nitro-quinoxaline-5-carbonyl)-methylamino]-acetic acid, tert-butyl ester;

3-[(2,3-Dimethoxy-6-methyl-7-nitro-quinoxaline-5-carbonyl)-amino]-propionic acid, tert-butyl ester;

(S)-2-[(2,3-Dimethoxy-6-methyl-7-nitro-quinoxaline-5-carbonyl)-amino]-3-phenylpropionic acid, tert-butyl ester;

2,3-Dimethoxy-6-methyl-7-nitro-quinoxaline-5-carboxylic acid dimethylamide;

2,3-Dimethoxy-6-methyl-7-nitro-quinoxaline-5-carboxylic acid methylamide;

2,3-Dimethoxy-6-methyl-7-nitro-quinoxaline-5-carboxylic acid benzylamide;

2,3-Dimethoxy-6-methyl-7-nitro-quinoxaline-5-carboxylic acid, 4-methoxy-benzylamide;

2,3-Dimethoxy-6-methyl-7-nitro-quinoxaline-5-carboxylic acid phenylamide;

2,3-Dimethoxy-6-methyl-7-nitro-quinoxaline-5-carboxylic acid (4-methoxyphenyl) amide;

(2,3-Dimethoxy-6-methyl-7-nitro-quinoxalin-5-yl)-piperazin-1-yl methanone;

[1,4]Diazepan-1-yl-(2,3-dimethoxy-6-methyl-7-nitro-quinoxalin-5-yl)methanone; and 2,3-Dimethoxy-6-methyl-7-nitro-quinoxaline-5-carboxylic acid, p-tolylamide.

For a description of bioisosteres see Annual Reports in Med. Chem., 1986;21:283; Chem. Soc. Reviews, 1979:563; Chemical Reviews, 1996;96:3147. Common bioisosteres are:

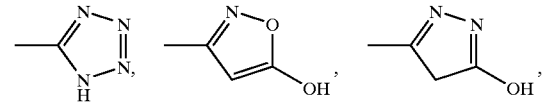

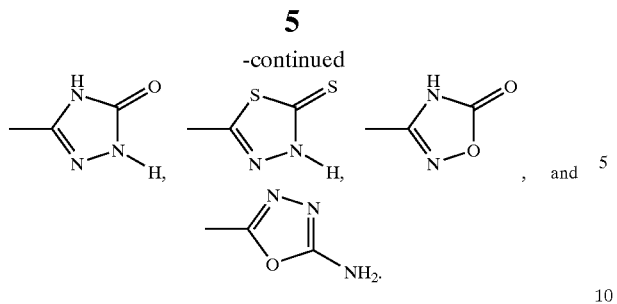

Common preferred heterocycles are:

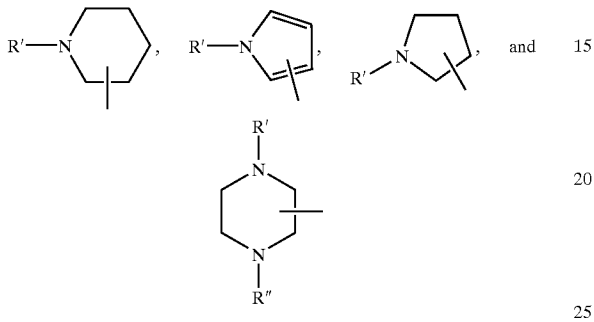

wherein R' and R" are independently H, alkyl, cycloalkyl, heterocycloalkyl, aralkyl, heteroaralkyl, aryl, heteroaryl, haloalkyl, $CO_2R_7$, $CONR_7R_8$, $(CH_2)_mSO_2NR_8R_9$, $C(O)R_7$, $SO_2CF_3$, and $CH_2SO_2R_7$.

Also described is a method for or treatment of neurodegenerative disorders including ALS, cerebral ischemia caused by cerebral trauma, stroke, hypoglycemia, heart attack, and surgery; anxiety and schizophrenia; and chronic neurodegenerative disorders such as Huntington's Disease, ALS, Parkinsonism, and Alzheimer's Disease. The compounds of this invention may also be employed as analgesics or in the treatment of epilepsy.

DETAILED DESCRIPTION

The present invention is concerned with compounds of Formula I. The compounds are prepared according to one or more of the following schemes.

SCHEME I

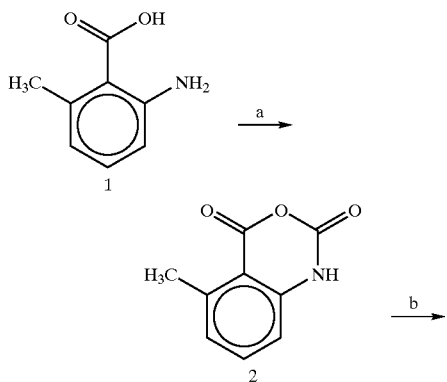

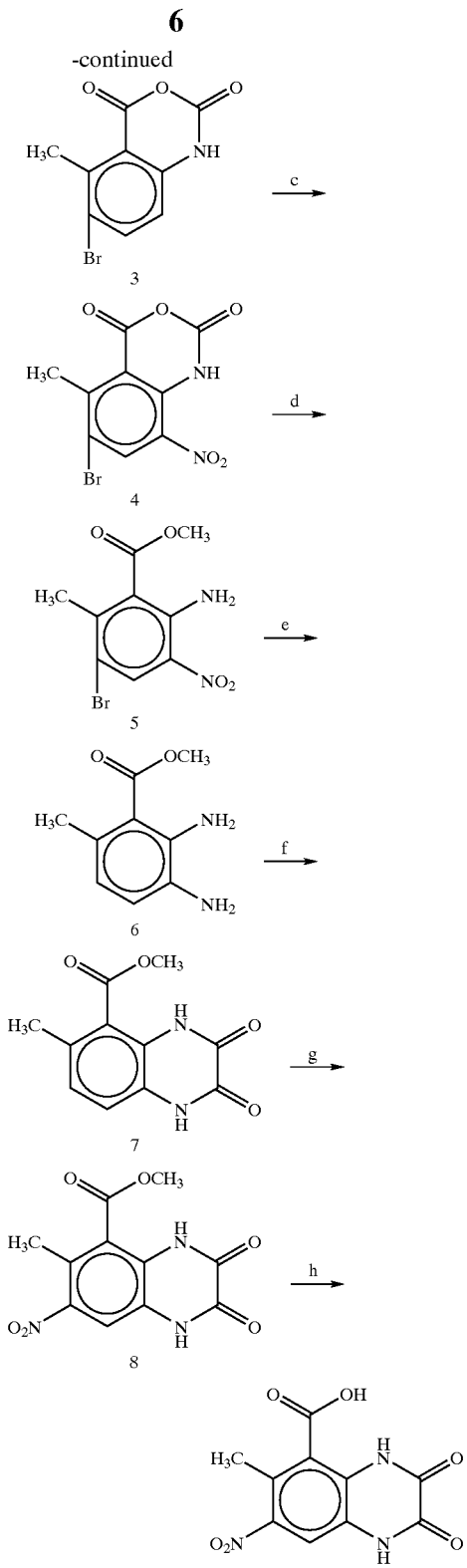

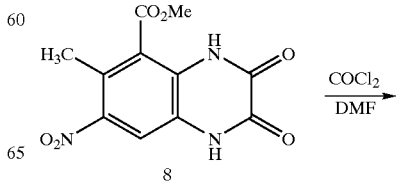

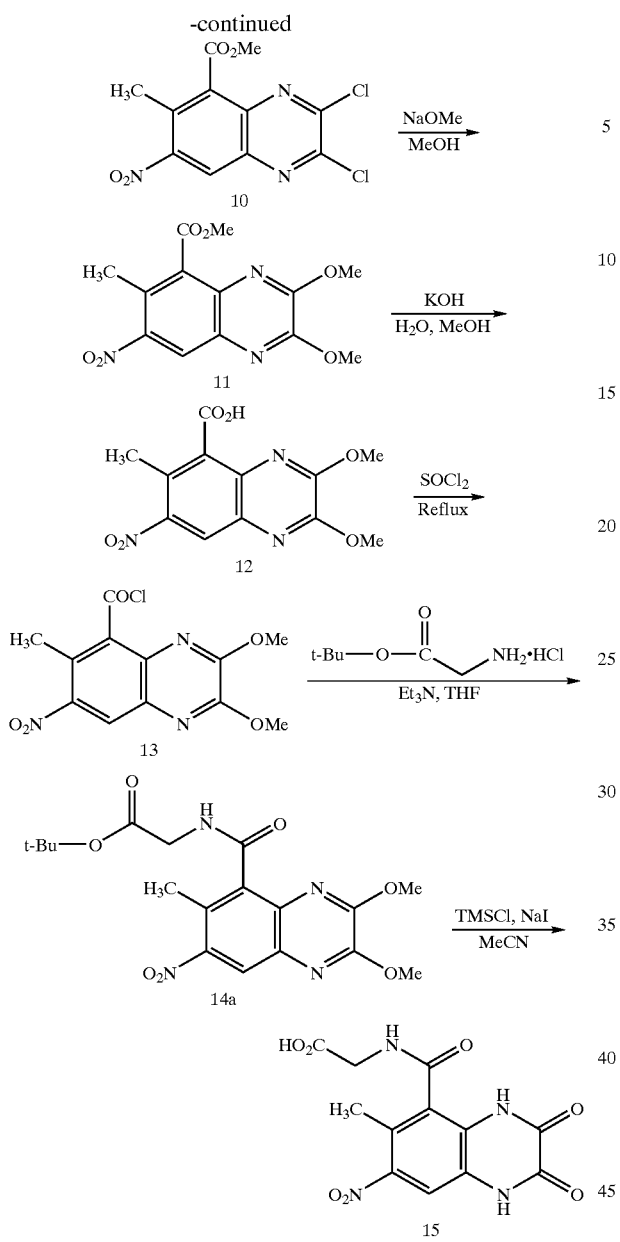
TABLE-continued
ANALOGS OF 14
| No. | R | Yield |
|---|---|---|
| 14b | t-Bu-O-C(O)-CH2-N(CH3)- | 74% |
| 14c | t-Bu-O-C(O)-CH2-CH2-NH- | 68% |
| 14d | t-Bu-O-C(O)-CH(CH2Ph)-NH- (S) | 57% |
| 14e | Me2N | 100% |
| 14f | MeNH | 76% |
| 14g | PhCH2NH | 84% |
| 14h | 4-MeO-C6H4-CH2-NH | 47% |
| 14i | PhNH | 62% |
| 14j | 4-MeO-C6H4-NH | 66% |
| 14k | piperazinyl (HN-N) | 86% |
| 14l | homopiperazinyl (HN-N, 7-membered) | 87% |

TABLE-continued
ANALOGS OF 14
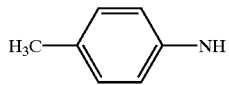
| No. | R | Yield |
|---|---|---|
| 14m | H₃C—⟨benzene⟩—NH | 65% |
SCHEME II
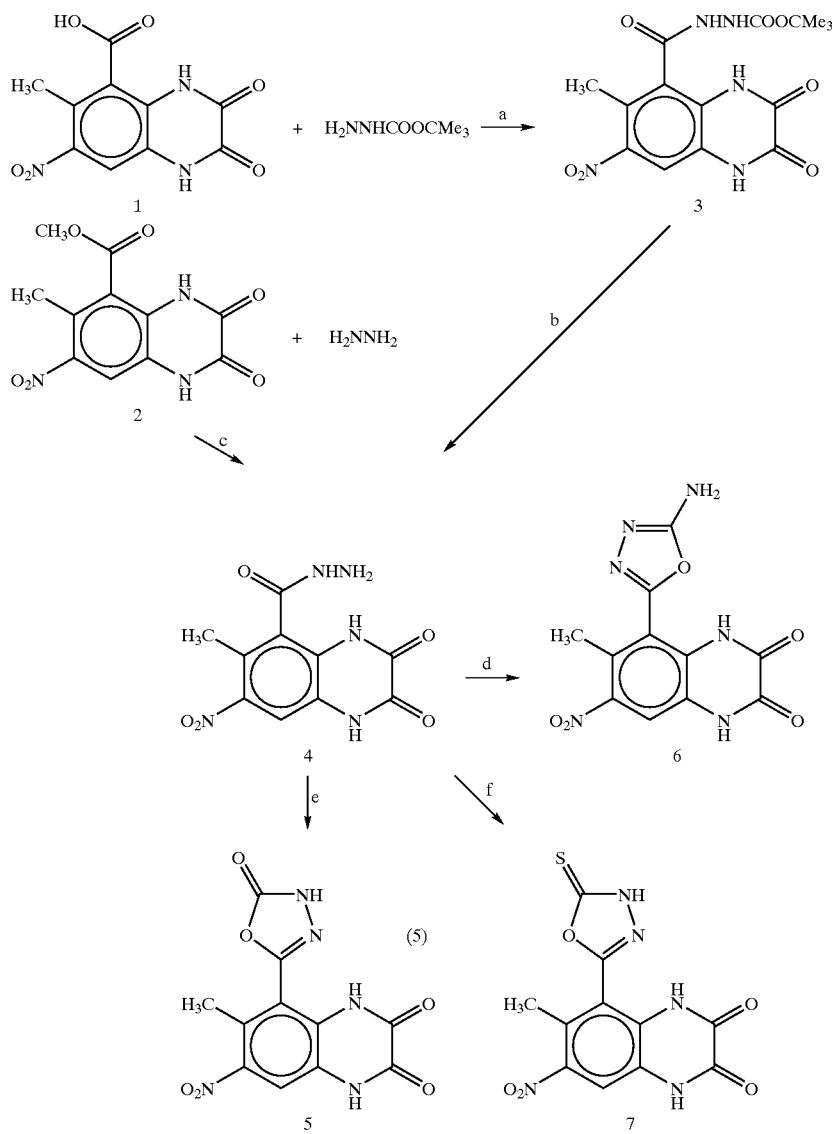

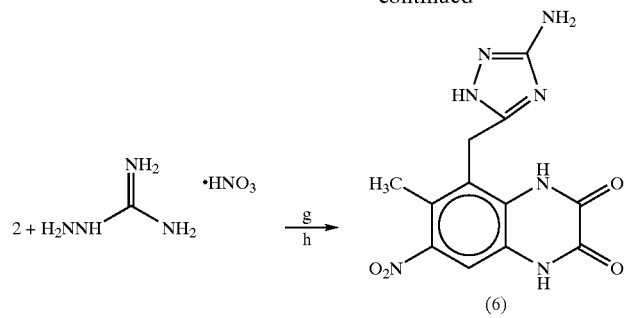
SCHEME III
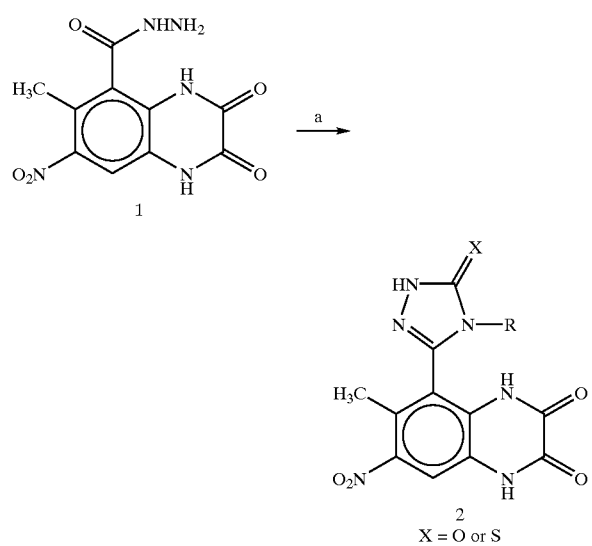
SCHEME IV
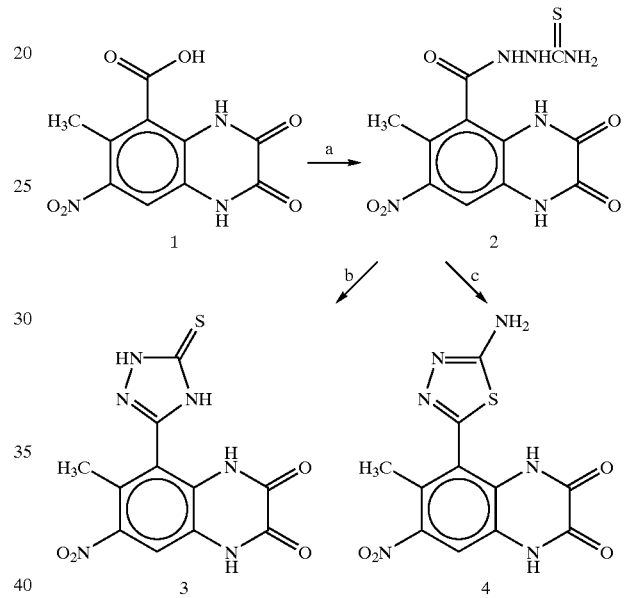
SCHEME V
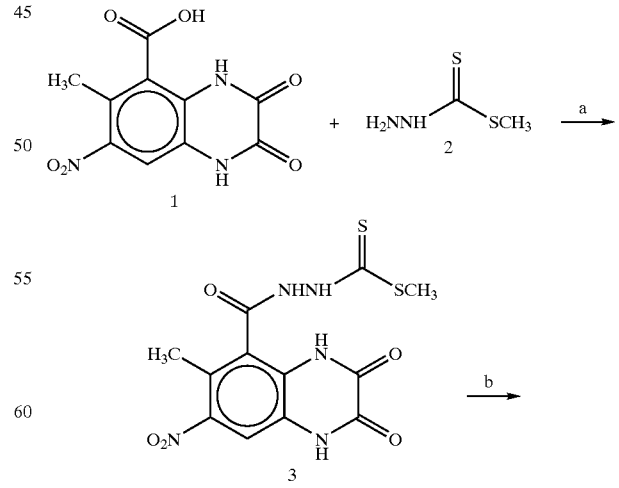

-continued
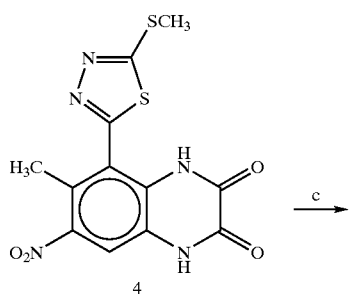
4
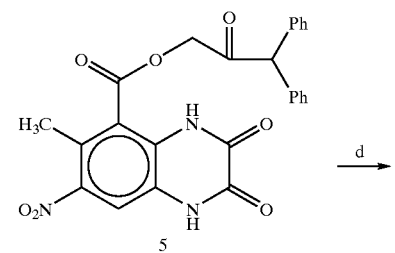
5
↓ c
↓ d
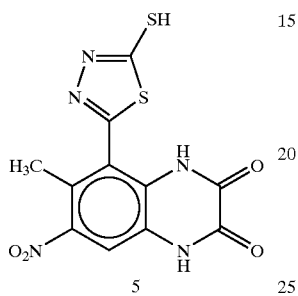
5
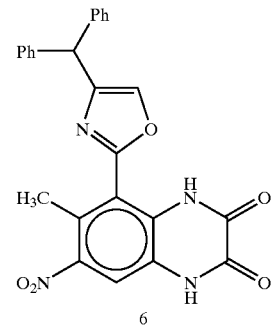
6
SCHEME VI
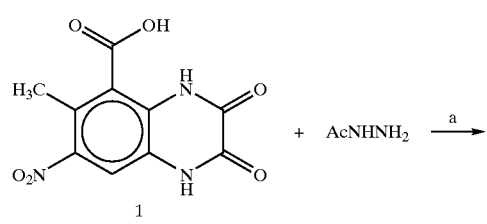
1
+ AcNHNH₂ →ᵃ
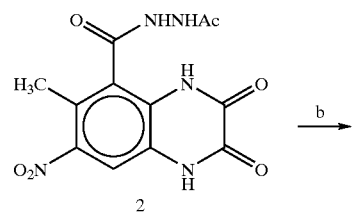
2
↓ b
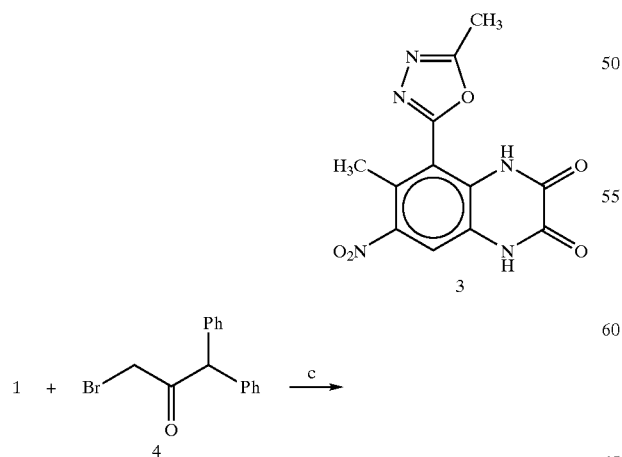
SCHEME VII
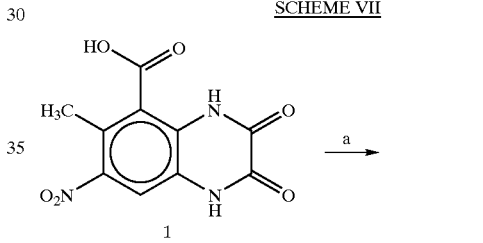
1
→ᵃ
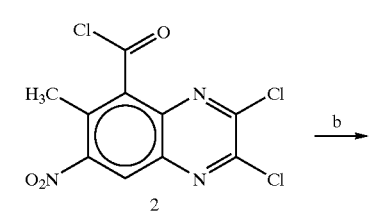
2
↓ b
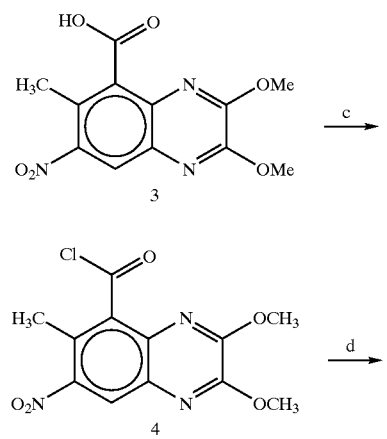

US 6,455,698 B1
15
-continued
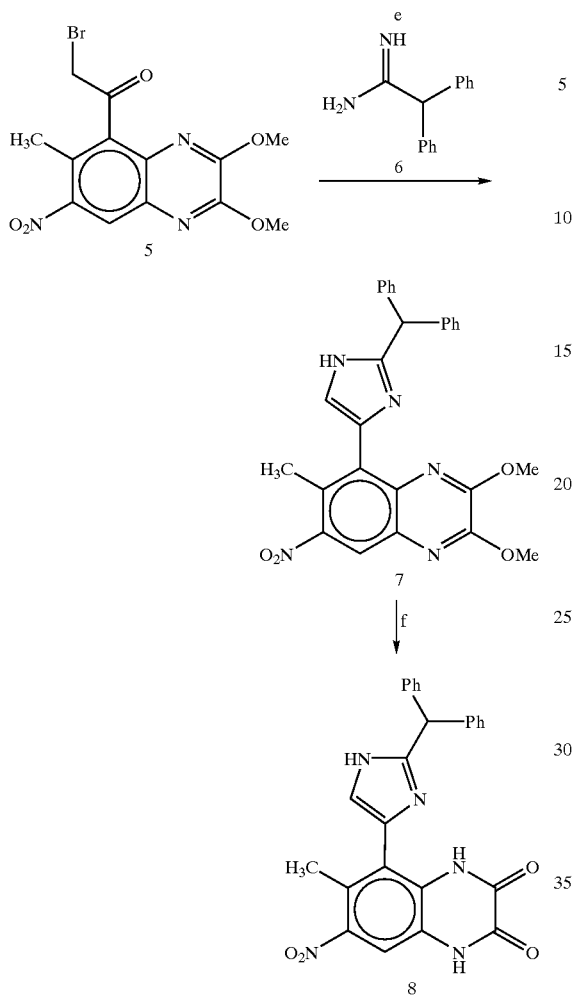
16
-continued
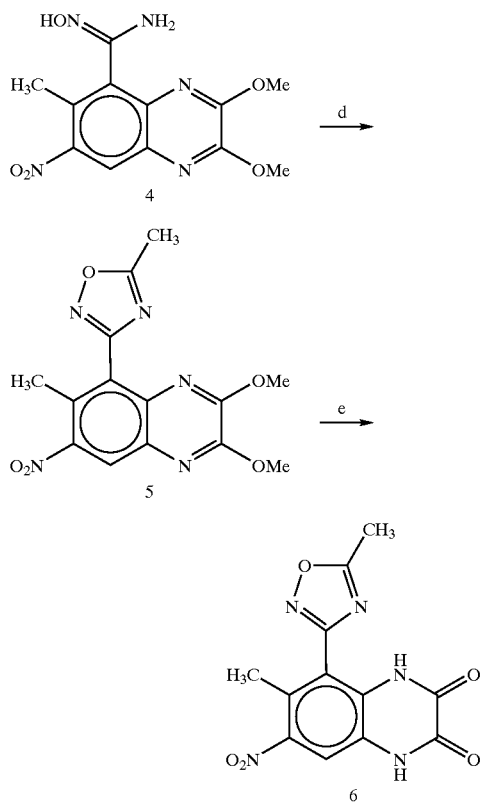
SCHEME IX
SCHEME VIII
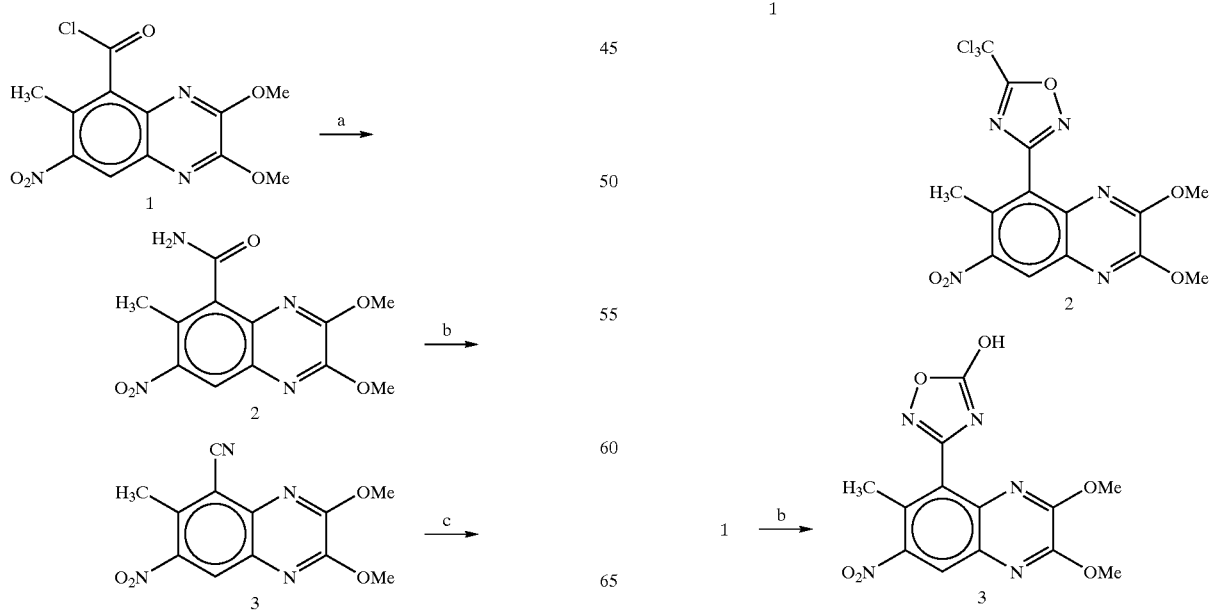

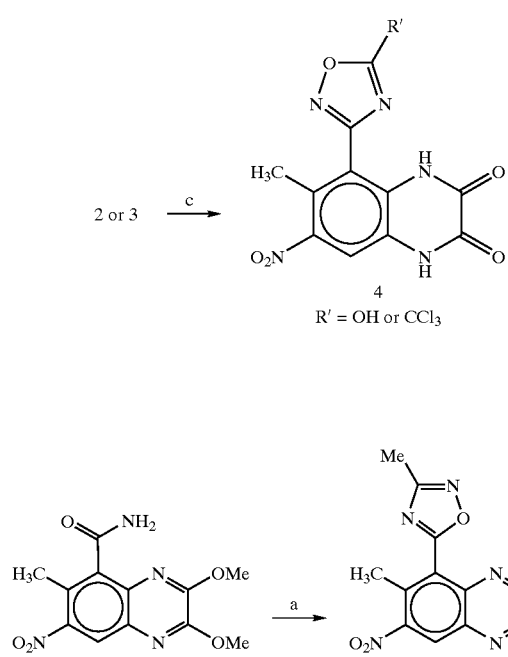
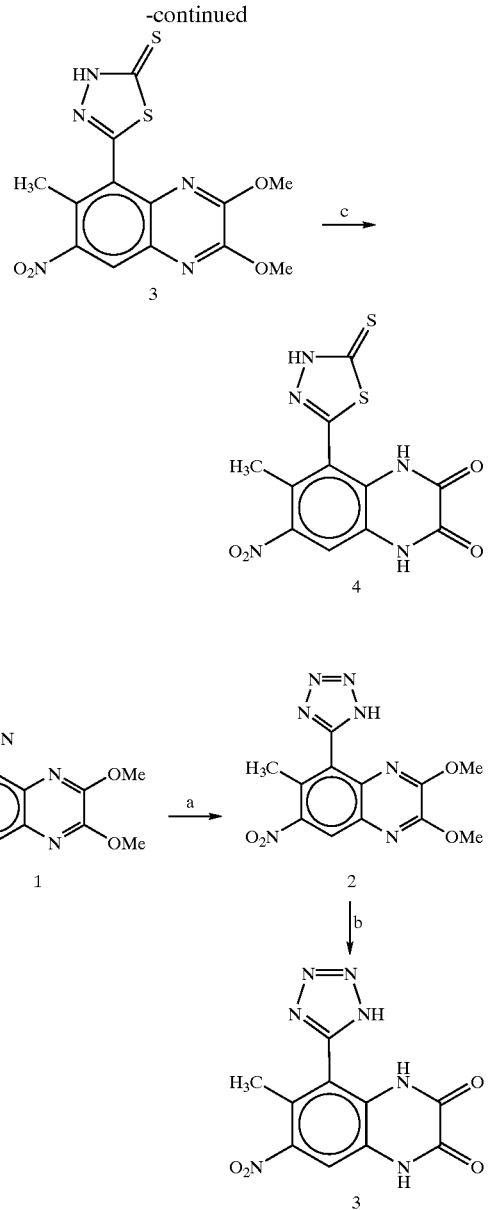
SCHEME XI
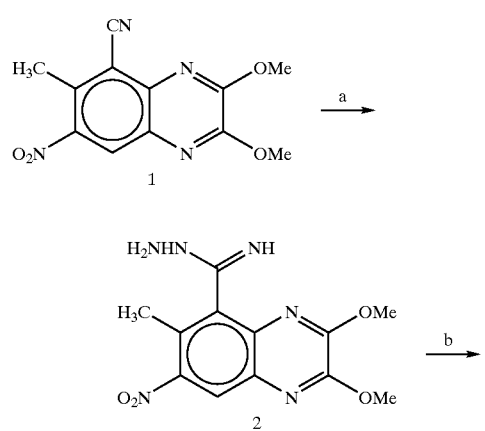
SCHEME XIII
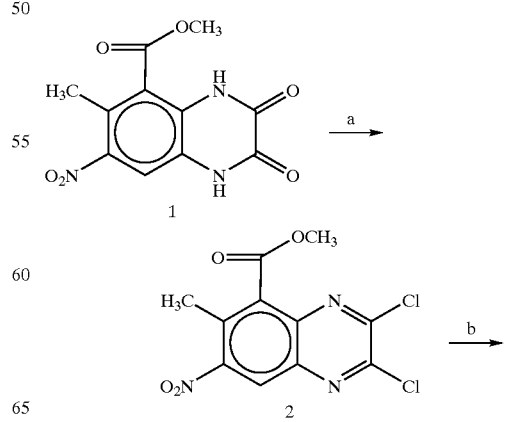

-continued
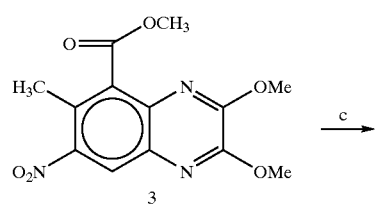
3
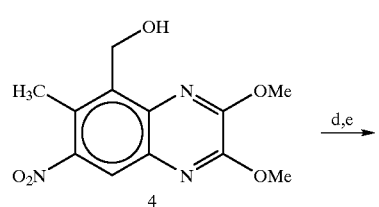
4
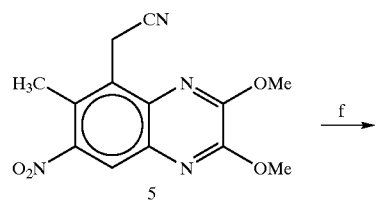
5
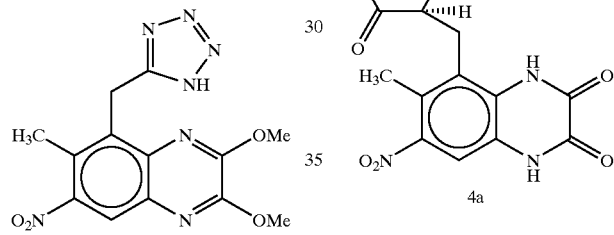
6
↓ g
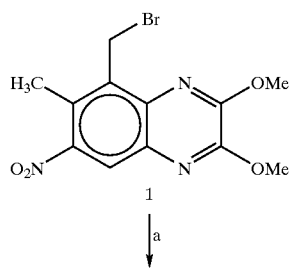
7
SCHEME XIV
-continued
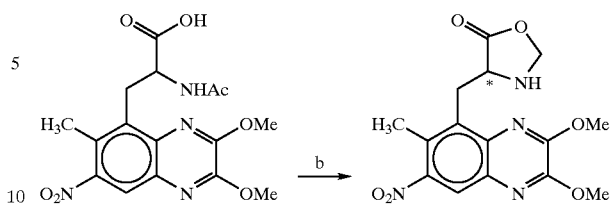
2
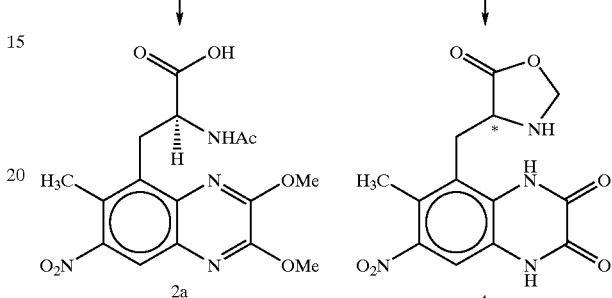
2a
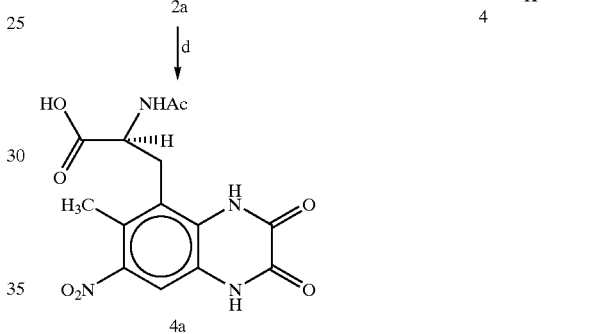
4a
SCHEME XV
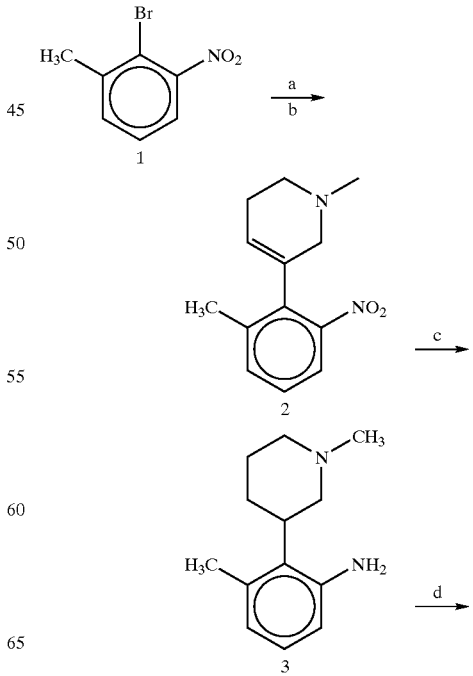

21
-continued
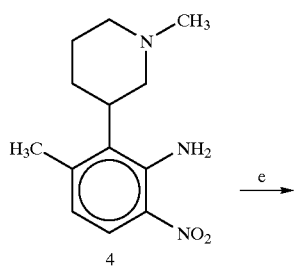
4
e →
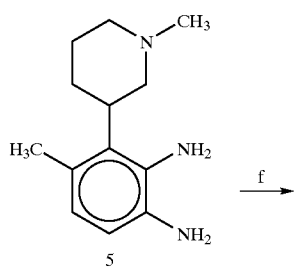
5
f →
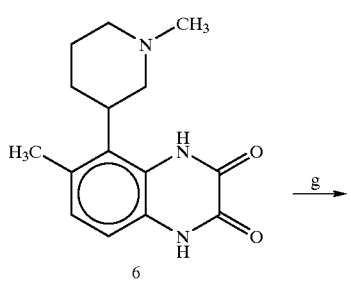
6
g →
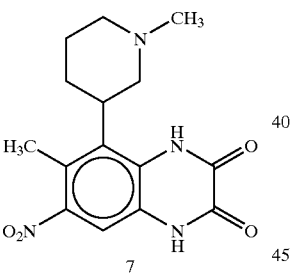
7
SCHEME XVI
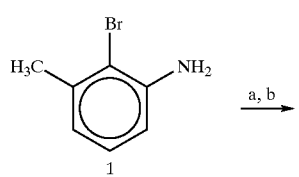
1
a, b →
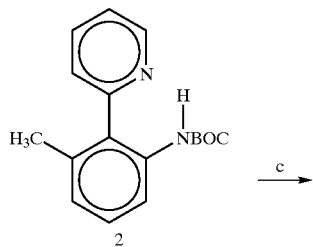
2
c →
22
-continued
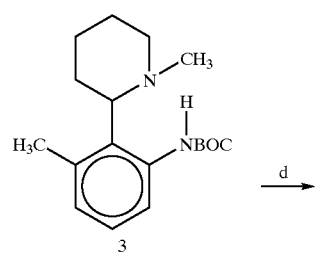
3
d →
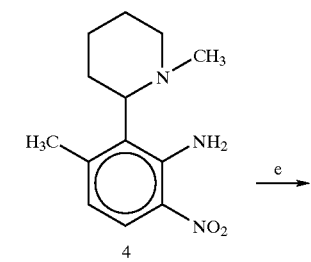
4
e →
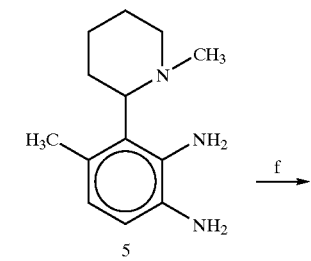
5
f →
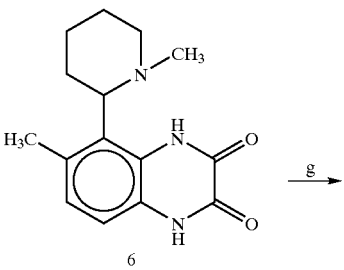
6
g →
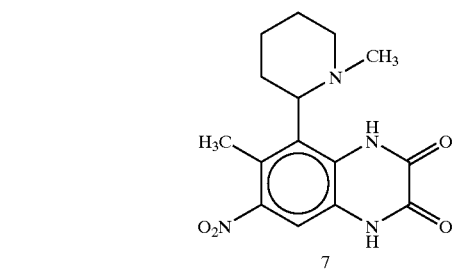
7
SCHEME XVII
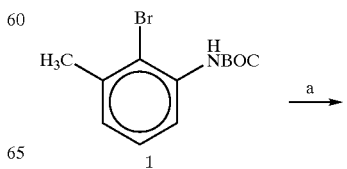
1
a →

23
-continued
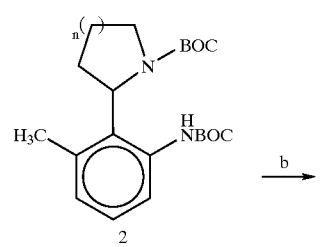
2
b →
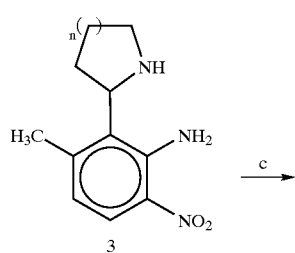
3
c →
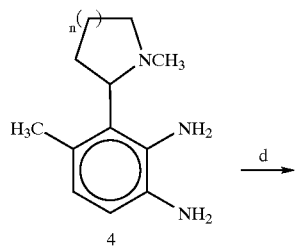
4
d →
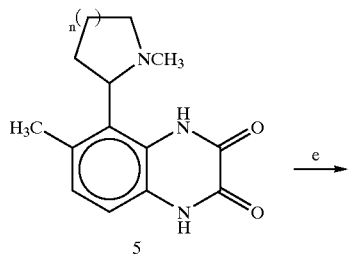
5
e →
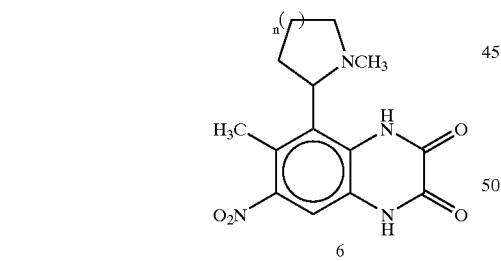
6
n = 1 or 2
24
-continued
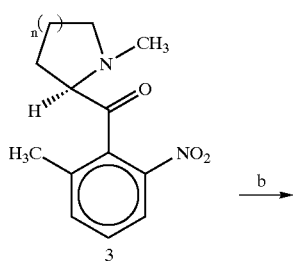
3
b →
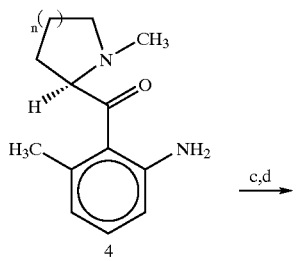
4
c,d →
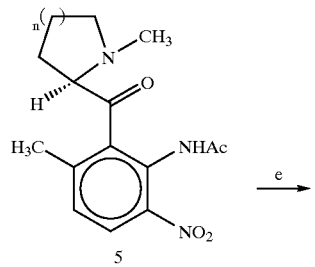
5
e →
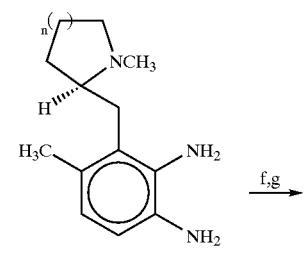
6
f,g →
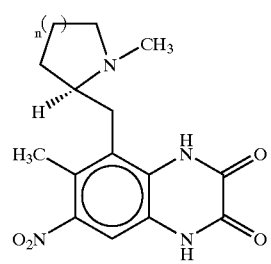
7
n = 1 or 2
SCHEME XVIII
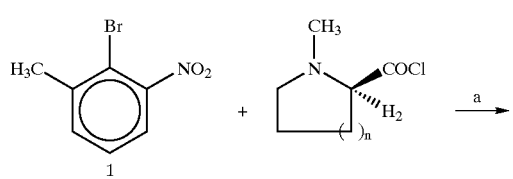
a →
SCHEME XIX
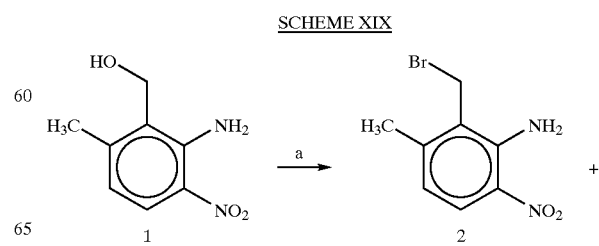

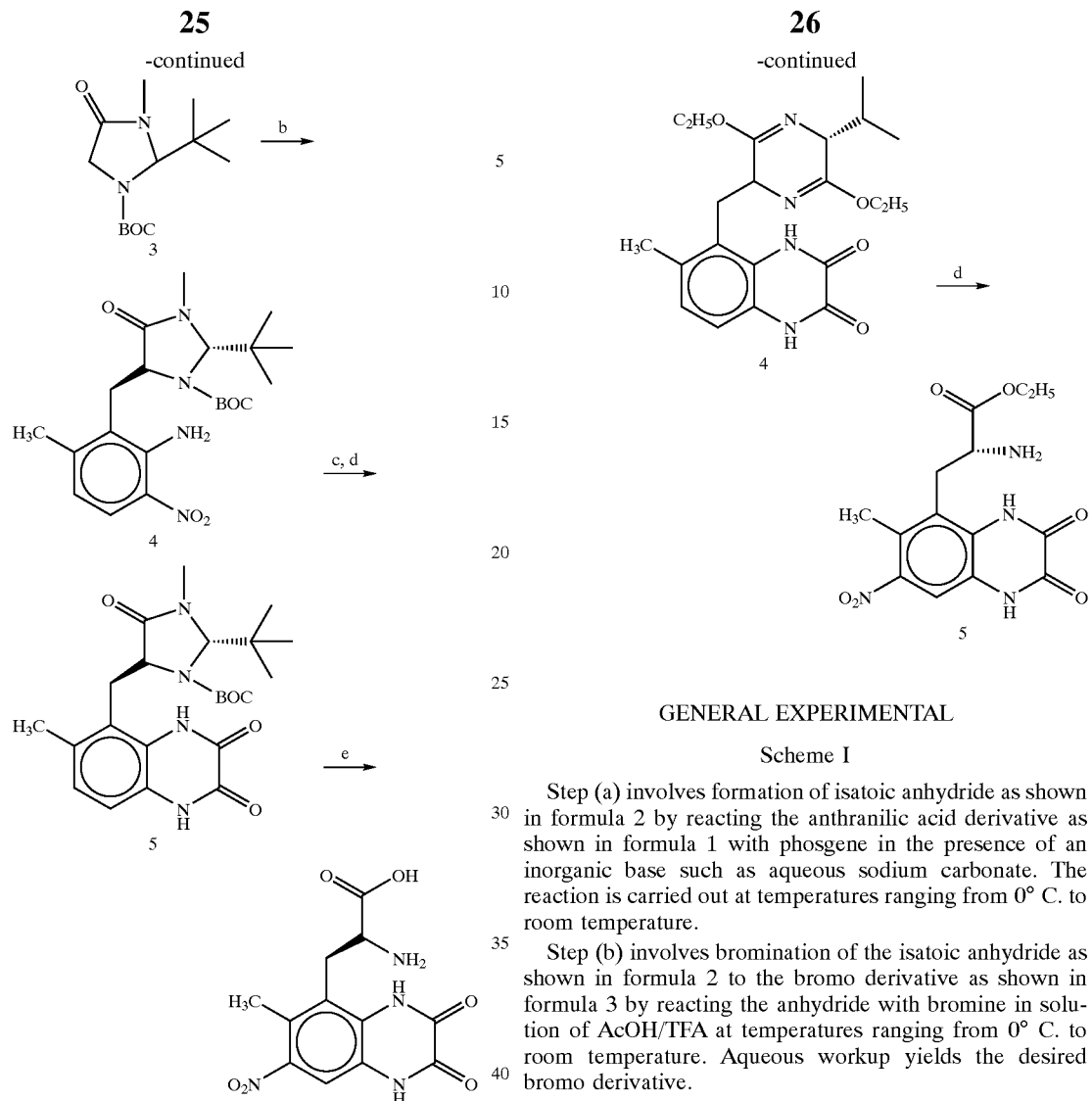

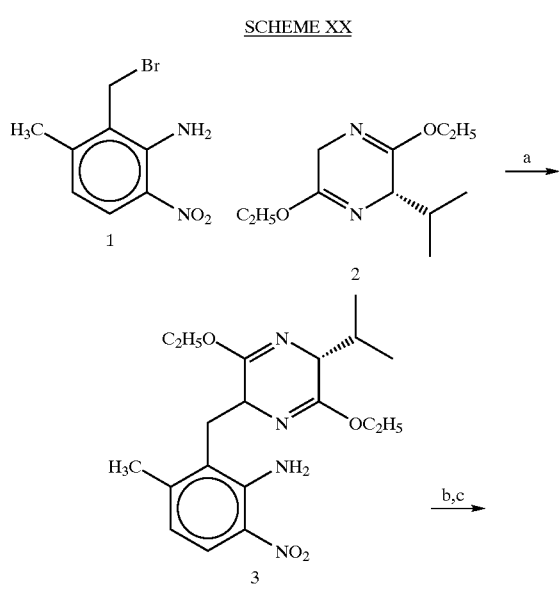

GENERAL EXPERIMENTAL

Scheme I

Step (a) involves formation of isatoic anhydride as shown in formula 2 by reacting the anthranilic acid derivative as shown in formula 1 with phosgene in the presence of an inorganic base such as aqueous sodium carbonate. The reaction is carried out at temperatures ranging from 0° C. to room temperature.

Step (b) involves bromination of the isatoic anhydride as shown in formula 2 to the bromo derivative as shown in formula 3 by reacting the anhydride with bromine in solution of AcOH/TFA at temperatures ranging from 0° C. to room temperature. Aqueous workup yields the desired bromo derivative.

Step (c) involves nitration of the isatoic anhydride shown in formula 3 with nitrating mixtures, preferably $KNO_3$/$H_2SO_4$, to give the nitro derivative as shown in formula 4. The reaction is carried out at temperatures ranging from 0° C. to room temperature, preferably doing the addition of the nitrating mixtures at 0° C.

Step (d) involves opening of the isatoic anhydride derivative as shown in formula 4 with an alcohol, preferably methanol. The reaction is carried out at reflux temperatures to give the desired methyl ester as shown in formula 5.

Step (e) involves catalytic reduction of the nitroaniline derivative as shown in formula 5 to the corresponding o-phenylenediamine derivative as shown in formula 6 using Raney Nickel as the catalyst with protic solvents, preferably methanol, under hydrogen atmosphere of up to 50 psi (in the presence of a base, preferably triethylamine).

Step (f) involves cyclization of the o-phenylenediamine derivative as shown in formula 6 to the corresponding quinoxaline-2,3-dione derivative as shown in formula 7. The diamine derivative is reacted with oxalic acid derivatives, preferably dimethyl oxalate, in a polar solvent such as methanol or ethereal solvent such as THF or aqueous acids such as hydrochloric acid. The reaction is carried out at reflux temperatures.

Step (g) involves nitration of the quinoxaline-2,3-dione derivative as shown in formula 7 to the corresponding 7-nitro derivative as shown in formula 8. The nitration is carried out with a nitrating mixture of $KNO_3/H_2SO_4$, and product is isolated by normal aqueous workup.

Step (h) involves hydrolysis of the ester derivative as shown in formula 8 to the corresponding acid derivative as shown in formula 9. The hydrolysis is carried out in the presence of a base, preferably KOH, in a water soluble solvent such as dioxane or methanol.

Scheme II

Step (a) involves the formation of protected hydrazide derivative as shown in formula 3 of the acid derivative as shown in formula 1 by coupling a monoprotected hydrazine derivative, preferably Boc-hydrazine, in the presence of coupling agents such as CDI or EDAC or via a reactive intermediate such as mixed anhydride, preferably via EDAC, in the presence of activating agents such as HOBt and DMAP in polar solvents such as dimethylformamide. The product is isolated by a normal aqueous workup.

Step (b) involves the deprotection of the hydrazine derivative shown in formula 3 to the corresponding hydrazide derivative shown in formula 4. The deprotection is carried out under acidic conditions such as aqueous HCl, or HCl saturated in organic solvent such as chloroform or dioxane. Alternatively, hydrazide derivative 4 is synthesized as shown in Step (c). Thus, compound shown in formula 4 is synthesized by reacting carboxylic acid ester derivative as shown in formula 2 with hydrazine with or without a solvent such as dioxane, THF or DMF, preferably neat, at temperatures ranging from room temperature to reflux, preferably reflux. The product is isolated by aqueous workup.

Step (d) involves cyclization of the hydrazide derivative as shown in formula 4 to the corresponding oxadiazole derivative as shown in formula 6 by reacting the hydrazide derivative with cyanogen bromide in the presence of inorganic bases such as sodium carbonate, sodium bicarbonate or potassium bicarbonate, preferably potassium bicarbonate, in polar solvents such as water, DMF or DMSO, preferably water, at temperatures ranging from room temperature to reflux, preferably elevated temperatures of 70° C. to 80° C.

Step (e) involves cyclization of the hydrazide derivative as shown in formula 4 to the corresponding oxadiazole derivative as shown in formula 5 by reacting the hydrazide derivative with bifunctional acylating agent such as phosgene or diethyl carbonate, preferably phosgene, in a hydrocarbon solvent such as benzene or toluene, or ethereal solvent such as THF, preferably THF, at temperatures ranging from room temperature to reflux, preferably room temperature.

Step (f) involves cyclization of the hydrazide derivative as shown in formula 4 to the corresponding oxadiazole derivative as shown in formula 7 by reacting the hydrazide derivative as shown in formula 4 with a disulfide agent such as carbon disulfide in the presence of inorganic bases such as sodium carbonate, sodium hydroxide or potassium carbonate or potassium hydroxide. Reaction is worked up under acidic conditions to give the desired product.

Steps (g) and (h) involve the cyclization of semicarbazide derivative formed in situ by reacting the ester derivative as shown in formula 2 with semicarbazide salt in the presence of an alkoxide base such as sodium methoxide or potassium t-butoxide, preferably sodium methoxide, in polar solvent such as methanol or butanol, preferably methanol, at temperatures ranging from room temperature to reflux. Acidic workup (Step h), preferably with methanolic HCl, would give the desired triazole derivative as shown in formula 6.

Scheme III

Step (a) involves the cyclization of hydrazide derivative as shown in formula 1 to the corresponding triazole derivative as shown in formula 2 with an isocyanate derivative such as methyl isocyanate in the presence of a polar solvent such as ethanol in the presence of a base such as sodium or potassium hydroxide. Acidic workup, preferably with aqueous HCl, gave the desired product.

Step (b) involves the conversion of oxadiazole derivative as shown in formula 3 to the corresponding triazole derivative as shown in formula 4 by reacting the oxadiazole derivative as shown in formula 3 with hydrazine in the presence of polar solvent such as ethanol at temperatures ranging from room temperature to reflux, preferably reflux, to give the product after acid workup, preferably with HCl.

Scheme IV

Step (a) involves the formation of the thiosemicarbazide derivative as shown in formula 2 by reacting the acid derivative as shown in formula 1 in the presence of coupling agents such as CDI or EDAC, or via activated acid derivatives such as anhydride or acid chloride; preferably EDAC in the presence of activating agent such as HOBt in polar solvents such as DMF at temperatures ranging from room temperature to 60° C., preferably room temperature.

Step (b) involves the cyclization of thiosemicarbazide derivative as shown in formula 2 to the corresponding triazole derivative as shown in formula 3 in the presence of inorganic bases such as potassium hydroxide or alkoxide bases such as sodium methoxide in polar solvents such as methanol. Alternatively, Step (c) shows that the semicarbazide derivative can be cyclized to form the corresponding thiadiazole derivative as shown in formula 4 under acidic conditions. The cyclization is carried out in the presence of acids such as methanesulfonic acid in polar solvents such as DMF at elevated temperatures, preferably around 100° C.

Scheme V

Step (a) involves the coupling of the acid derivative as shown in formula 1 with the hydrazine derivative as shown in formula 2 in the presence of coupling agents such as CDI or EDAC, preferably EDAC, in the presence of activating agents such as HOBt in polar solvents such as DMF at temperatures ranging from room temperature to 40° C., preferably room temperature.

Step (b) involves cyclization of the hydrazide derivative as shown in formula 3 to the corresponding thiadiazole derivative as shown in formula 4 under acidic conditions, preferably p-toluenesulfonic acid, or under oxidative conditions using perchloric acid in acetic anhydride. The thiomethyl derivative as shown in formula 4 is deprotected as shown in Step (c), preferably using sodium thiomethoxide in polar solvents such as DMF at temperatures ranging from room temperature to 100° C. to give the corresponding thiol derivative as shown in formula 5.

Scheme VI

Step (a) involves the coupling of the acid derivative as shown in formula 1 with the acetyl hydrazine derivative in the presence of coupling agents such as CDI or EDAC, preferably CDI, in the presence of activating agents such as HOBt in polar solvents such as DMF to give hydrazide derivative as shown in formula 2.

Step (b) involves cyclization of the hydrazide derivative as shown in formula 2 to the corresponding oxadiazole derivative as shown in formula 3 via silylation of hydrazide derivative, preferably with hexamethyldisilazane, followed by cyclization involving desilylation in the presence of a base such as TBAF in a high boiling solvent such as chlorobenzene at temperatures ranging from room temperature to reflux, preferably at reflux.

Step (c) involves alkylation of the alkali metal salt such as sodium or potassium salt of the acid derivative as shown in formula 1 with alpha-bromo ketone derivative as shown in formula 4 in the presence of a base such as tetrabutylammonium bromide in a high boiling solvent such as toluene or chlorobenzene, preferably toluene. The ester is isolated by normal aqueous workup.

Step (d) involves cyclization of the ester as shown in formula 5 to the corresponding oxazole derivative as shown in formula 6 in the presence of a base like ammonium acetate in an acidic solvent such as acetic acid.

Scheme VII

Step (a) involves chlorination of the 5-carboxylic acid derivative of quinoxaline-2,3-dione as shown in formula 1 to the corresponding chloro derivative shown in formula 2, using chlorinating agents such as phosphoryl chloride or phosphous pentachloride or thionyl chloride, preferably a mixture of phosphoryl chloride and phosphorus pentachloride. The reaction is carried out at temperatures ranging between 80° C. to reflux, preferably reflux. Volatile material is evaporated and the reaction mixture quenched over ice followed by aqueous inorganic base workup using aqueous solution of sodium bicarbonate or sodium carbonate, preferably sodium bicarbonate. The product is isolated on adjusting the pH to 6 using acids such as acetic acid or HCl, preferably acetic acid.

Step (b) involves methoxylation of the 2,3-dichloroquinoxaline derivative as shown in formula 2 to the corresponding 2,3-dimethoxy compound as shown in formula 3. The reaction is carried out using an alkali metal alkoxide, preferably sodium methoxide, in hydroxylated solvent such as methanol at temperatures ranging from room temperature to reflux, preferably reflux, and product isolated by aqueous workup.

Step (c) involves chlorination of the 5-carboxylic acid derivative as shown in formula 3 to the corresponding acid chloride derivative as shown in formula 4 using chlorinating agents such as oxalyl chloride, thionyl chloride or phosphorus trichloride, preferably thionyl chloride at temperatures ranging from room temperature to reflux, preferably reflux.

Step (d) involves generation of the α-haloketone as shown in formula 5 from the 5-carboxylic acid chloride derivative as shown in formula 4 via a diazoketone generated by reacting the acid chloride with diazomethane. The diazoketone intermediate on treatment with acids like HBr or HCl, preferably HBr, gave the corresponding α-bromomethyl ketone as shown in formula 5.

Step (e) involves cyclization of the α-haloketone as shown in formula 5 to the corresponding imidazolyl derivative as shown in formula 7 by reacting the compound shown in formula 5 with an amidine derivative, preferably with benzhydrylamidine derivative as shown in formula 6 in a chlorinated solvent such as dichloromethane or chloroform, preferably chloroform (*Heterocycles*, 1996;42:517).

Step (f) involves deprotection of the imino ether moieties in formula 7 to the corresponding amide derivative as shown in formula 8. The reaction is carried out using trimethylsilyl iodide or trimethylsilyl chloride/KI mixture or inorganic acids such as aqueous HCl or HBr, preferably 5N HCl at temperatures ranging from room temperature to 100° C., preferably 80° C.

Scheme VIII

Step (a) involves generation of the amide as shown in formula 2 from the acid chloride derivative as shown in formula 1 by reacting the acid chloride with ammonia in a sealed tube. The reaction is also carried out in an ethereal solvent such as dioxane or THF, preferably dioxane, and bubbling in gaseous ammonia.

Step (b) involves dehydration of the amide as shown in formula 2 to give the corresponding cyano derivative as shown in formula 3. The reaction is carried out using dehydrating agents such as polyphosphoric acid with or without a solvent.

Step (c) involves generation of the amidine derivative as shown in formula 4 by treating the cyano derivative as shown in formula 3 with hydroxylamine hydrochloride in the presence of an inorganic base such as potassium carbonate or sodium carbonate in an alcoholic solvent such as methanol or ethanol, preferably ethanol.

Step (d) involves cyclization of the amidine derivative as shown in formula 4 to the corresponding oxadiazole derivative as shown in formula 5 by reacting the amidine derivative with an acid chloride, preferably with acetyl chloride, in the presence of an organic base such as pyridine or triethylamine, preferably pyridine, using base as the solvent at temperatures ranging from room temperature to reflux, preferably reflux.

Step (e) involves the cleavage of the imino ether functionality as shown in formula 5 to the corresponding amide derivative as shown in formula 6. The cleavage is carried out in the presence of reagents such as trimethylsilyl iodide or trimethylsilyl chloride/KI, or inorganic acids such as HCl or HBr, preferably aqueous HCl.

Scheme IX

Step (a) involves cyclization of the hydroxyamidine derivative as shown in formula 1 to the corresponding substituted oxadiazole derivative as shown in formula 2 by reacting the hydroxyamidine derivative with an acid chloride, preferably with trichloroacetylchloride, in the presence of an organic acid such as acetic acid or trichloroacetic acid, preferably trichloroacetic acid, at temperatures ranging from room temperature to reflux, preferably above 100° C., *J. Med. Chem.*, 1994;37:2421.

Step (b) involves cyclization of the hydroxyamidine derivative as shown in formula 1 to the corresponding oxadiazoline derivative as shown in formula 3 by reacting the hydroxyamidine derivative with a reactive bifunctional acylating agent such as ethyl chloroformate or phosgene, preferably ethyl chloroformate, in the presence of inorganic bases such as potassium carbonate in polar solvents such as acetone at temperatures ranging from room temperature to reflux, preferably reflux. Alternatively, the cyclization can be carried out by reacting hydroxyamidine derivative with diethyl carbonate in the presence of alkali metal bases such as sodium or potassium ethoxide in an alcoholic solvent such as ethanol at temperatures ranging from room temperature to reflux, preferably reflux.

Step (c) involves cleavage of the imino ethers in compounds shown in formula 2 or 3 to give the corresponding amide derivatives as shown in formula 4. The deprotection can be carried out in the presence of silyl agents such as trimethylsilyl iodide or trimethylsilyl chloride/KI mixture or in the presence of inorganic acids such as aqueous HCl or HBr.

Scheme X

Step (a) involves the cyclization of the amide derivative as shown in formula 1 to the corresponding oxadiazole derivative as shown in formula 2 by reacting the amide initially with a diketo compound such as dimethylacetamide dimethyl acetal to give the corresponding acylamidine derivative in situ. The acylamidine derivative on treatment with hydroxylamine hydrochloride in the presence of inorganic bases such as sodium bicarbonate or sodium hydroxide or sodium acetate, preferably sodium hydroxide, in an aqueous solution, gave the cyclized product as shown in formula 2.

Step (b) involves the cleavage of the imino ethers in compound shown in formula 2 to the corresponding amide derivative as shown in formula 3 using conditions described in Scheme IX, Step (c).

Scheme XI

Step (a) involves the generation of the aminoamidinyl intermediate as shown in formula 2 from the 5-cyano-2,3-dimethoxy-quinoxaline derivative as shown in formula 1 by treating the cyano derivative with hydrazine in the presence of a base like sodium hydride using ethereal solvent such as THF or dioxane, preferably THF. The reaction can be carried out at temperatures ranging from room temperature to reflux, preferably reflux.

Step (b) involves cyclization of the aminoamidine derivative as shown in formula 2 to the corresponding thiadiazole derivative as shown in formula 3 by treating compound 2 with carbon disulfide at temperatures ranging from room temperature to reflux, preferably reflux.

Step (c) involves deprotection of the imino ethers in compound shown in formula 3 using conditions described in Scheme IX, Step (c).

Scheme XII

Step (a) involves the formation of the tetrazole derivative as shown in formula 2 by reacting the corresponding cyano derivatives as shown in formula 1 with tri-n-butyltin azide in an ethereal solvent such as dioxane or THF, preferably dioxane, at temperatures ranging from room temperature to reflux preferably around 60° C.

Step (b) involves deprotection of the imino ethers in compound shown in formula 2 using conditions discussed in Scheme IX, Step (c) to give the amide derivative shown in formula 3.

Scheme XIII

Step (a) involves the chlorination of the quinoxaline-2,3-dione derivative as shown in formula 1 to the corresponding 2,3-dichloro derivative as shown in formula 2 using conditions discussed in Scheme VII, Step (a).

Step (b) involves methoxylation of the dichloro derivative shown in formula 2 to the corresponding 2,3-dimethoxy compound as shown in formula 3 using alkali metal alkoxide, preferably sodium methoxide, in alcoholic solvent such as methanol at temperatures ranging from room temperature to reflux, preferably reflux.

Step (c) involves reduction of the ester moiety in the compound shown in formula 3 to the corresponding hydroxymethyl derivative shown in formula 4 using a borohydride reagent, preferably lithium borohydride, in an alcoholic solvent, preferably ethanol, at temperatures ranging from room temperature to 50° C., preferably room temperature.

Step (d) involves bromination of the hydroxymethyl derivative shown in formula 4 using brominating agents such as HBr or phosphorus tribromide or thionyl bromide, preferably HBr, in solvents such as acetic acid.

Step (e) involves converting the bromomethyl derivative to the corresponding cyanomethyl derivative as shown in formula 5 using alkali metal cyanide, preferably potassium cyanide, in polar solvents such as DMSO or DMF, preferably DMSO.

Step (f) involves a cycloaddition reaction involving the cyanomethyl derivative shown in formula 5 with a dipolarophile such as tri-n-butyltin azide to give the tetrazole derivative as shown in formula 6. The reaction can be carried out as described in Scheme XII, Step (a).

Step (g) involves deprotection of the imino ethers as shown in formula 6 to the corresponding amide derivative as shown in formula 7 as described in Scheme IX, Step (c).

Scheme XIV

Step (a) involves alkylation of the bromomethyl derivative shown in formula 1 with diethylacetamidomalonate sodium salt, generated by treating diethylacetamidomalonate with sodium hydride in an ethereal solvent such as THF or polar solvent such as DMF to give the amino acid precursor, which on treatment with a base such as aqueous sodium hydroxide in alcoholic solvent such as ethanol gave the desired N-acetyl-amino acid derivative as shown in formula 2.

Step (b) involves cyclization of the amino acid intermediate as shown in formula 2 to the corresponding oxazolidinone derivative as shown in formula 3 by treating the amino acid intermediate with formaldehyde in acidic solvent such as acetic acid in the presence of catalytic p-toluenesulfonic acid. On aqueous workup, the desired oxazolidinone is obtained (Walter M. W., et al., *Tetrahedron Letters*, 1995;36:7761).

Step (c) involves the optional resolution step of the stereoisomers of the amino acid derivative shown in formula 2. The resolution is carried out by using hog kidney acylase in aqueous solution at pH 7.5. The D-isomer is isolated and crystallized. The optically pure amino acid derivative, as shown in formula 2a, can also be used to synthesize the oxazolidinone derivative shown in formula 3 as a single enantiomer.

Step (d) involves deprotection of the imino ethers as shown in formulas 2a and 4 to the corresponding amide derivatives as shown in formulas 4 and 4a. The deprotection can be carried out as described in Scheme IX, Step (c).

Scheme XV

Step (a) involves the reaction of the organomagnesium salt of 2-bromo-3-nitrotoluene as shown in formula 1, prepared by the reaction of compound 1 and fresh magnesium turnings in ether, with an amino ketone such as 1-methyl-3-piperidone derivative in an ethereal solvent such as diethyl ether or THF or dioxane. The reaction mixture is quenched with aqueous ammonium chloride solution (Step b), and the crude product is heated to about 100° C. with a protic solvent such as acetic acid or HCl. The tetrahydropyridinyl derivative as shown in formula 2 is isolated as a free base on quenching the reaction with saturated sodium bicarbonate or ammonia solution.

Step (c) involves the reduction of the tetrahydropyridinyl derivative as shown in formula 2 to give the corresponding piperidinyl derivative as shown in formula 3. The reduction is carried out under catalytic hydrogenation conditions using Pd/C (5% to 20%), preferably 20%, and hydrogen gas at 50 psi in a hydroxylated solvent such as methanol.

Step (d) involves acetylation of the amino group in compound shown in formula 3 followed by nitration and deprotection to give the nitroaniline derivative as shown in formula 4. The acetylation is carried out by heating the solution of compound 3 in acetic anhydride to reflux or by treating a solution of compound 3 in a solvent such as dichloromethane or THF, preferably dichloromethane with acetyl chloride in the presence of a base such as triethylamine or pyridine and a catalytic amount of DMAP. In the case of pyridine as the base, the amine is dissolved in pyridine. The nitration is carried out using nitrating mixtures such as potassium nitrate and sulfuric acid or nitric acid in acetic anhydride, preferably nitric acid in acetic anhydride. Removal of the acetyl group is done by treatment with an inorganic base such as sodium hydroxide in hydroxylated solvent such as methanol or water.

Step (e) involves reduction of the o-nitroaniline derivative as shown in formula 4 to the corresponding o-phenylenediamine intermediate as shown in formula 5. The reduction is carried out under catalytic hydrogenation conditions using Raney Nickel or Pd/C as the catalysts and hydrogen gas under pressures of up to 50 psi in alcoholic solvents such as methanol. The reduction is also carried out under metal/acid conditions such as Fe/HCl or Sn/HCl, preferably Fe/HCl.

Step (f) involves formation of quinoxaline-2,3-dione derivative as shown in formula 6 by reacting the o-phenylenediamine derivative shown in formula 5 with an alpha-dicarbonyl derivative such as oxalyl chloride or dimethyl oxalate or oxalic acid, preferably dimethyl oxalate, in an ethereal solvent such as THF or protic solvent such as methanol or aqueous HCl, preferably THF.

Step (g) involves nitration of the quinoxaline-2,3-dione derivative shown in formula 6 to give the corresponding nitro derivative as shown in formula 7 using reagents such as $KNO_3/H_2SO_4$ or $HNO_3$ or nitronium tetrafluoroborate, preferably $KNO_3/H_2SO_4$.

Scheme XVI

Step (a) involves protection of the amino group of the aniline derivative as shown in formula 1. The preferred protecting group is Boc and is incorporated by treating the aniline derivative with Boc anhydride in the presence of an aqueous base such as sodium hydroxide or sodium carbonate, preferably sodium carbonate.

Step (b) involves the coupling of 2-chloropyridine with the N-Boc aniline derivative in the presence of a base such as n-BuLi in an ethereal solvent such as anhydrous THF. The coupling is carried out at temperatures ranging from 0° C. to room temperature to give the product as shown in formula 2.

Step (c) involves reduction of the pyridyl ring in the compound shown in formula 2 to give the corresponding reduced compound as shown in formula 3. Initially, the pyridinyl moiety is quaternized with an alkylating agent such as methyl iodide or methyl triflate, preferably methyl iodide, in the presence of solvent such as THF or methanol. The quaternary salt is then reduced to the tetrahydro stage using borohydride reducing agents such as sodium borohydride or sodium cyanoborohydride, preferably sodium borohydride, in solvents such as ethanol. The tetrahydropyridyl ring is fully reduced to the piperidinyl ring via catalytic hydrogenation using Pd/C as the catalyst and hydrogen gas (up to 50 psi) in solvents such as THF or ethanol.

Step (d) involves nitration of the piperidinyl compound shown in formula 3 to give the corresponding nitroaniline derivative as shown in formula 4. The nitration is carried out using conditions described in Step (d) of Scheme XV.

Step (e) involves reduction of the nitroaniline derivative shown in formula 4 to the corresponding o-phenylenediamine derivative as shown in formula 5. The reduction is carried out as described in Step (e) in Scheme XV.

Step (f) involves formation of the quinoxaline-2,3-dione derivative as shown in formula 6 by reacting oxalic acid derivative with the o-phenylenediamine as shown in formula 5. The reaction conditions are described in Step (f), Scheme XV.

Step (g) involves nitration of the quinoxaline-2,3-dione derivative as shown in formula 6 to give the corresponding nitro derivative as shown in formula 7. The reaction conditions are described in Step (g) in Scheme XV.

Scheme XVII

Step (a) involves Pd catalyzed coupling of bromobenzene derivative shown in formula 1 with 2-lithio-N-Boc-pyrrolidino or N-Boc-piperidino compound as shown in formula 2 generated in situ by reacting N-Boc pyrrolidine or piperidine with sec-BuLi in a solvent such as THF to give the corresponding cyclic amine derivative as shown in formula 2. The reaction is carried out as reported in the literature by Dieter, et al., *Tetrahedron Letters*, 1995;36:3613–3616. The reaction is carried out in the presence of catalytic amounts of CuCN and $Pd[(p-OCH_3—Ph)_3P]_4$ or $PdCl_2(PPh_3)_2$.

Step (b) involves nitration of the aniline derivative shown in formula 2 to give the corresponding o-nitroaniline derivative as shown in formula 3. The conditions for nitration are described in Step (d), Scheme XV.

Step (c) and (d) involve the reduction of the o-nitroaniline derivative to the corresponding o-phenylenediamine derivative as shown in formula 3 and cyclization of the o-phenylenediamine derivative as shown in formula 4 to the corresponding quinoxaline-2-3-dione derivative as shown in formula 5, respectively. The conditions for both these steps have been described in Steps (e) and (f) of Scheme XV, respectively.

Step (e) involves nitration of the quinoxaline-2,3-dione derivative as shown in formula 5 to the corresponding nitro derivative as shown in formula 6. The conditions for the nitration are described in Step (g) of Scheme XV.

Scheme XVIII

Step (a) involves coupling of the bromobenzene derivative as shown in formula 1 with amino acid chloride as shown in formula 2 via generation of the organomagnesium salt using fresh magnesium turnings in a solvent such as ether. The ketone derivative as shown in formula 3 is isolated on quenching the reaction with aqueous ammonium chloride followed by normal aqueous workup (Macor J. E., et al., *J. Organic Chem.*, 1994;59:7496).

Step (b) involves the reduction of the nitro group of the nitrobenzene derivative as shown in formula 3 under catalytic hydrogenation conditions to give the corresponding aniline derivative as shown in formula 4. The preferred catalyst is Raney Nickel, and the solvent is preferably methanol and hydrogen gas at around 50 psi.

Steps (c) and (d) involve acetylation of the aniline derivative as shown in formula 4 followed by nitration to give the o-nitroaniline derivative as shown in formula 5. The conditions for acetylation and nitration are described in Step (d) of Scheme XV.

Step (e) involves deprotection of the amino group and reduction of the keto nitroaniline derivative as shown in formula 5 to the corresponding o-phenylenediamine derivative as shown in formula 6. The acetyl group is saponified using an aqueous base such as sodium or potassium hydroxide, preferably sodium hydroxide. The reduction is carried out using LAH as a reducing agent in an ethereal solvent such as anhydrous THF. Alternatively, the keto group can be reduced under Wolff-Kishner conditions, i.e., via the hydrazone formation followed by the catalytic (Ra-Ni) reduction of the nitro group.

Steps (f) and (g) involve the formation of the quinoxaline-2,3-dione derivative followed by nitration of the quinoxaline-2,3-dione derivative as shown in formula 7 from the o-phenylenediamine derivative as shown in formula 6. The conditions for the quinoxaline-2,3-dione formation and nitration are described in Steps (f) and (g) of Scheme XV.

Scheme XIX

Step (a) involves formation of the benzyl bromide derivative as shown in formula 2 from the benzyl alcohol derivative as shown in formula 1 from the benzylalcohol derivative as shown in formula 1. The bromination is carried out using brominating agents such as phosphorus tribromide, thionyl bromide or $CBr_4/PPh_3$, preferably $CBr_4/PPh_3$, in an ethereal solvent such as ether or THF, preferably ether.

Step (b) involves alkylation of the N-Boc imidazolone derivative as shown in formula 3 with the benzyl bromide derivative as shown in formula 2. The reaction involves generation of an anion using a lithium base such as LDA in ethereal solvent such as THF followed by addition of the benzyl bromide solution (Harding M. M., et al., *Tetrahedron Asymmetry*, 1994;5: 1793–1804).

Steps (c) and (d) involve reduction of the o-nitroaniline derivative as shown in formula 4, followed by the cyclization of the o-phenylenediamine derivative to the corresponding quinoxaline-2,3-dione derivative as shown in formula 5. The conditions for reduction and cyclization are described in Steps (e) and (f) of Scheme XV, respectively.

Step (e) involves the nitration of the quinoxaline-2,3-dione derivative and simultaneous hydrolytic ring opening of the imidazolone side-chain as shown in formula 5 to the corresponding 7-nitro-quinoxaline-2,3-dione derivative as shown in formula 6. The conditions for nitration are described in Step (g) of Scheme XV.

Scheme XX

Step (a) involves alkylation of the anion of 2,3-diethoxy pyrazine (Schollkopf chiral auxiliary) derivative as shown in formula 2 with benzyl bromide derivative as shown in formula 1. The anion is generated using a lithium base, preferably n-BuLi, and the reaction can be carried out as described earlier by Cook, et al., *Synthetic Communications*, 1995;25:3883–3900 to give the product as shown in formula 3.

Steps (b) and (c) involve reduction of the o-nitroaniline derivative as shown in formula 2 to the o-phenylenediamine derivative and formation of the corresponding quinoxaline-2,3-dione derivative as shown in formula 4, respectively. The conditions for reduction and cyclization are described in Steps (e) and (f) in Scheme XV, respectively.

Step (d) involves the nitration of the quinoxaline-2,3-dione derivative as shown in formula 3 to the corresponding 7-nitro derivative as shown in formula 4. During nitration the 2,5-diethoxypyrazine side-chain is hydrolyzed to give the amino acid side-chain as shown in formula 5. The conditions for nitration are as described in Step (g) of Scheme XV.

The aforementioned abbreviations have the following meanings:

| | |
|---|---|
| Boc | tertiary Butyloxycarbonyl |
| CDI | 1,1'-Carbonyldimidazole |
| CBZ | Benzyloxycarbonyl |
| DEAD | Diethyl azodicarboxylate |
| DEE | Diethyl ether |
| DMAP | 4-Dimethylaminopyridine |
| DMF | Dimethylformamide |
| DMSO | Dimethyl sulfoxide |
| EDAC | Ethyl-3-(3-dimethylamino)-propylcarbodiimide |
| FMOC | 9-Fluorenylmethyloxycarbonyl |
| HOBt | 1-Hydroxybenzotriazole |
| LAH | Lithium Aluminum Hydride |
| NMP | n-Methyl pyrrolidone |
| TEA | Triethylamine |
| TFA | Trifluoroacetic acid |
| THF | Tetrahydrofuran |

Some preferred compounds are shown below. The compounds are preferably $NO_2$ derivatives for $R_4$.

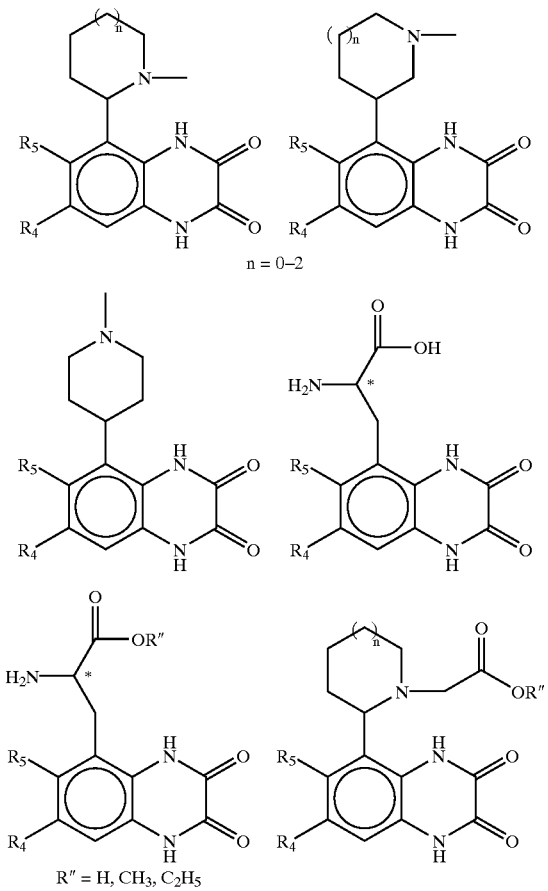

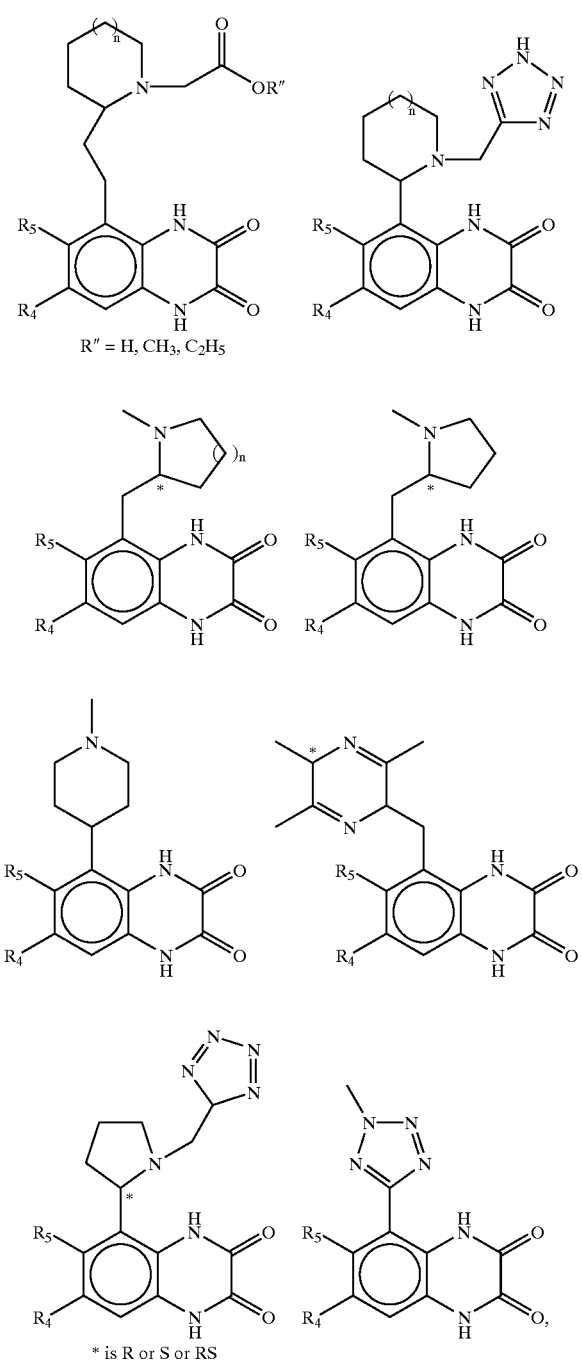

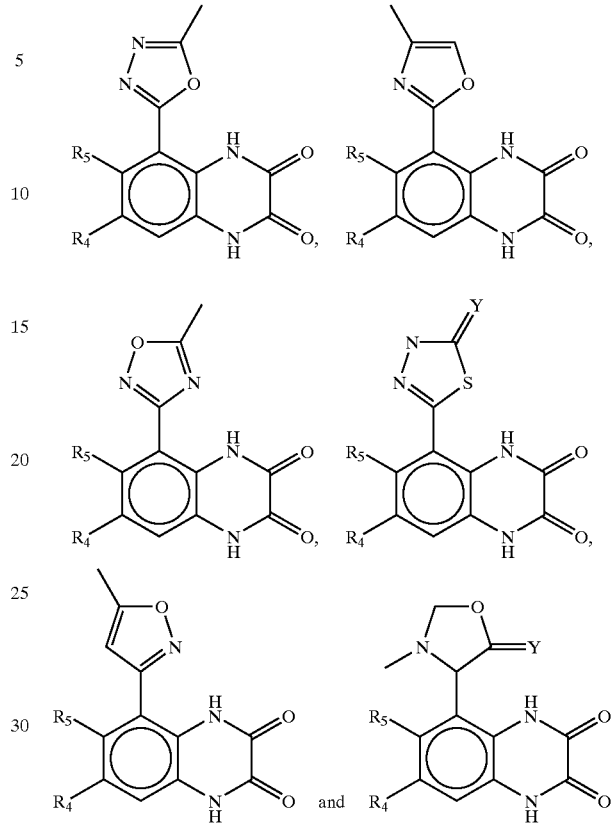

wherein Y is oxygen or sulfur.

Some of the compounds of Formula I are capable of further forming both pharmaceutically acceptable acid addition and/or base salts. These forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and bicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. Pharma. Sci.*, 1977;66:1).

The acid addition salts of said basic compounds can be prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts can be formed with metals or amines, such as alkali and alkaline earth metals or organic amines. Examples of such metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see Berge, Supra, 1977).

The base addition salts of said acidic compounds can be prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

In the compounds of Formula I the amino acid derivative is an ester, an amide, a hydrazide, or a semicarbazide. The term "alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "carboxyalkyl" means alkyl as above and attached to a carboxy group.

The term "phosphoroalkyl" means alkyl as above and attached to a phosphoro group.

The term "phosphonoalkyl" means alkyl as above and attached to a phosphono group.

The term "alkenyl" means a straight or branched unsaturated hydrocarbon radical having from 3 to 6 carbon atoms and includes, for example, 2-propenyl, 1-butenyl, 2-butenyl, 1-pentenyl, 2-pentenyl, 3-methyl-3-butenyl, 1-hexenyl, 2-hexenyl, 3-hexenyl, and the like.

"Alkoxy" or "thioalkoxy" is O-alkyl or S-alkyl of from 1 to 6 carbon atoms as defined above for "alkyl".

The term "aryl" means an aromatic radical which is a phenyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined for alkyl, or 1,3-benzodioxol-5-yl.

The term "aralkyl" means aryl and alkyl as defined above and includes but is not limited to benzyl, 2-phenylethyl, and 3-phenylpropyl; a preferred group is phenyl.

The term "heteroaryl" means a heteroaromatic radical which is 2-, 3-, or 4-pyridinyl, 2-, 4-, or 5-pyrimidinyl, 2- or 3-thienyl, isoquinolines, quinolines, imidazolines, pyrroles, indoles, and thiazoles.

"Halogen" is fluorine, chlorine, bromine, or iodine.

The term "haloalkyl" means halogen and alkyl as defined above, for example, but not limited to, trifluoromethyl and trichloromethyl. "Alkylaryl" means aryl as defined above and alkyl as defined above, for example, but not limited to benzyl, 2-phenylethyl, 3-phenylpropyl; a preferred group is benzyl.

The term "heterocycloalkyl" means a nonaromatic ring with from 4 to 7 members, with up to 4 heteroatoms for example, N, O, and S.

Common amino acid moiety means the naturally occurring l-amino acids, unnatural amino acids, substituted $\upsilon$, K, $\Lambda$ amino acids and their enantiomers.

Common amino acids are: Alanine, $\upsilon$-alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

Modified and unusual amino acids are as would occur to a skilled chemist and are, for example, but not limited to:

10,11-Dihydro-5H-dibenzo[a,d]cyclohepten-5-yl)glycine or l-Amino- 10,11-dihydro-5H-dibenzo[a,d]cycloheptene-5-acetic acid (Para-phenyl) phenylalanine;

3,3-Diphenylalanine;

3-Hydroxyproline;

4-Hydroxyproline;

N-Methylphenylalanine;

N-Methylaspartic acid;

N-Methylisoleucine;

N-Methylvaline;

Norvaline;

Norleucine;

Ornithine;

2-Aminobutyric acid;

2-Amino4-pentanoic acid (Allylglycine);

$N^G$-Nitroarginine;

2-Amino-3-(2-amino-5-thiazole)propanoic acid;

2-Amino-3-cyclopropanepropanoic acid (Cyclopropylalanine);

Cyclohexylalanine (Hexahydrophenylalanine);

N-Methylcyclohexylalanine (N-Methylhexahydrophenylalanine);

2-Amino-4,4(RS)-epoxy-4-pentanoic acid;

$N^{im}$-2,4-Dinitrophenylhistidine;

2-Aminoadipic acid;

2-Amino-5-phenylpentanoic acid (Homophenylalanine);

Methionine sulfoxide;

Methionine sulfone;

3-(1'-Naphthyl)alanine;

3-(2'-Naphthyl)alanine;

2-Amino-3-cyanopropanoic acid (Cyanoalanine);

Phenylglycine;

2-Aminopentanoic acid (Propylglycine);

2-Amino-6-(1-pyrrolo)-hexanoic acid;

2-Amino-3-(3-pyridyl)-propanoic acid (3-Pyridylalanine);

1,2,3,4-Tetrahydro-3-isoquinolinecarboxylic acid;

2-Amino-3-(4-thiazolyl)-propanoic acid;

O-Tertiarybutyl-tyrosine;

O-Methyl-tyrosine;

O-Ethyl-tyrosine;
N$^{in}$-Formyl-tryptophan;
5H-Dibenzo[a,d]cycloheptenyl glycine;
9H-Thioxanthenyl glycine; and
9H-Xanthenyl glycine.

The compounds of the present invention can be prepared and administered in a wide variety of routes of administration such as parenteral, oral, topical, rectal, inhalation and the like. Formulations will vary according to the route of administration selected. Examples are oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. The following dosage forms may comprise as the active component, a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier can be a finely divided solid which is in a mixture with the finely divided active component.

In tablets, the active component can be mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component can be dispersed homogeneously therein, as by stirring. The molten homogenous mixture can be then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted for example from about 0.1 mg to 200 mg, preferably about 0.5 mg to 100 mg according to the particular application and the potency of the active component. The composition can, if desired, also contain other compatible therapeutic agents.

In therapeutic use as agents for the treatment of neurological disorders, the compounds utilized in the pharmaceutical methods of this invention can be administered at an initial dosage of about 0.01 mg to about 200 mg/kg daily. A daily dose range of about 0.01 mg to about 50 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

Having described the invention herein, listed below are preferred embodiment or working examples wherein all temperatures are degrees Centigrade and all parts are parts by weight unless otherwise indicated.

EXAMPLES

EXAMPLE 1

Scheme I procedure is followed as indicated below:
5-Methyl-isatoic Anhydride (2)

To an aqueous solution of anthranilic acid (100 g, 0.66 mol) and sodium carbonate (0.7 mol) a solution of phosgene in toluene (362 mL, 1.93 M, 0.7 mol) was added dropwise under vigorous stirring. The reaction becomes a suspension and is stirred for additional 8 hours and filtered. The residue was treated with aqueous Na$_2$CO$_3$ and filtered. Washed with water (4×150 mL) and dried.

Yield: 88.4 g, 75.4%. MS (CI) m/z=178 (M+1).
6-Bromo-5-methyl-isatoic Anhydride (3)

To a suspension of 5-methyl-isatoic anhydride (9.2 g, 0.052 mol) in a mixture of glacial acetic acid (60 mL) and TFA (30 mL), bromine (9.9 g, 0.062 mol) was added under stirring at 5° C. Reaction mixture warmed to room temperature and stirred~5 hours. Poured in cold water and yellow ppt filtered and washed with water and dried. Yield: 12.09 g, 90%.

MS (CI) m/z=257 (M+1).
6-Bromo-5-methyl-8-nitro-isatoic Anhydride (4)

To a solution of 6-bromo-5-methyl-isatoic anhydride (12.03 g, 0.047 mol) in sulfuric acid (80 mL), potassium nitrate (5.05 g, 0.05 mol) was added at room temperature under vigorous stirring. After stirring approximately 8 hours, reaction mixture was poured over ice. The aqueous suspension was stirred for 0.5 hour and filtered and washed with water (4×100 mL) and dried. Yield 10.8 g, 76%. MS (CI) m/z=302 (M+1).

Methyl-2-amino-5-bromo-6-methyl-3-nitrobenzoate (5)

A mixture of 6-bromo-5-methyl-8-nitro-isatoic anhydride (17.48 g, 0.0580 mol) in MeOH (180 mL) was heated at reflux for 3 hours. After standing at 0° C. for 2 to 3 hours, the precipitated product (5) was collected and washed with MeOH. Yield 12.24 g, 73%.

2,3,-Diamino-6-methylbenzoate (6)

A mixture of methyl-2-amino-5-bromo-6-methyl-3-nitrobenzoate (5) (12.24 g, 0.0423 mol) and 20% Pd on C (1.0 g) in 1:1 MeOH:THF (400 mL) with triethylamine (5.9 mL, 0.042 mol) was hydrogenated for 2 hours under a hydrogen pressure of 50 psi. The catalyst was filtered off (celite), and the filtrate was concentrated. The residue was taken up in EtOAc, and the organic layer was washed with a minimal amount of water. The organic layer was dried over sodium sulfate, filtered, and concentrated to give 7.62 g (100%) product (6).

MS (APCI) m/z=181 (M+1).

Synthesis of 6-Methyl-2,3-dioxo-1,2,3,4-tetrahydro-quinoxaline-5-carboxylic Acids Methyl Ester (7)

A solution of 2,3-diamino-6-methylbenzoic acid, methyl ester (compound 6) (1.14 g, 6.35 mmol) and dimethyl oxalate (3.34 g, 28.5 mmol) in MeOH (30 mL) was refluxed for 6 days. Upon cooling to room temperature, the precipitated product was collected and washed with a small amount of MeOH to give 1.02 g (69%).

MS (APCI) m/z=235 (M+1).

Synthesis of 6-Methyl-7-nitro-2.3-dioxo- 1,2,3,4-tetrahydro-quinoxaline-5-carboxylic Acid Methyl Ester (8)

To a solution of 6-methyl-2,3-dioxo- 1,2,3,4-tetrahydro-quinoxaline-5-carboxylic acid, methyl ester (1.11 g, 4.74 mmol) in conc. $H_2SO_4$ (15 mL) at room temperature was added in one portion with vigorous stirring potassium nitrate (0.529 g, 5.23 mmol). The reaction mixture was stirred for 23 hours and poured over ice. The precipitated product was thoroughly washed with water upon collection to give 1.28 g (97%).

MS (CI) m/z=280 (M+1).

Synthesis of 6-Methyl-7-nitro-2,3-dioxo-1.2,3 4-tetrahydro-quinoxaline-5-carboxylic Acid (9)

To a suspension of 6-methyl-7-nitro-2,3-dioxo- 1,2,3,4-tetrahydro-quinoxaline-5-carboxylic acid, methyl ester (0.80 g, 2.87 mmol) in THF (50 mL) was added aqueous 1.0N NaOH (4.3 mL, 4.3 mmol), and the reaction mixture was refluxed for 23 hours. The product is precipitated upon acidification with conc. HCL and recrystallized from water to give 0.73 g (96%).

MS (APCI) m/z=266 (M$^+$+1).

2.3-Dichloro-6-methyl-7-nitro-quinoxaline-5-carboxylic Acid Methyl Ester (10)

To a suspension of 6-methyl-7-nitro-2,3-dioxo-1,2,3,4-tetrahydro-quinoxaline-5-carboxylic acid methyl ester (8) (5.85 g, 0.021 mol) in anhydrous N,N-dimethylformamide (60 mL) under an atmosphere of nitrogen was added dropwise a 20% phosgene solution in toluene 34.03 mL (0.068 mol). During the course of addition a mild exotherm resulted, and all undissolved material went into solution. After addition was complete (approximately 10 minutes), the reaction mixture was stirred at room temperature for 22 hours and concentrated. The residue was triturated with methanol and an off-white crystalline solid precipitated, 5.98 g (90%), mp 155–157° C.; $^1$H NMR (CDCl$_3$): δ 8.48 (s, 1H), 4.05 (s, 3H), 2.59 (s, 3H); MS (APCI): m/z 317 (M$^+$+H)$^+$, 315 (M–H)$^+$. Anal. Calcd. for C$_{11}$H$_7$Cl$_2$N$_3$O$_4$: C, 41.80; H, 2.23; N, 13.29; Cl, 22.43. Found: C, 41.74; H, 2.04; N, 13.23; Cl, 22.15.

2.3-Dimethoxy-6-methyl-7-nitro-quinoxaline-5-carboxylic Acid Methyl Ester (11)

To a solution of sodium metal (washed with hexane) 119 mg (5.19 mmol) dissolved in anhydrous methanol (15 mL) under an atmosphere of nitrogen at room temperature was added portionwise 2,3-dichloro-6-methyl-7-nitro-quinoxaline-5-carboxylic acid methyl ester (10, caution: exothermic) 655 mg (2.07 mmol). After the addition was complete (approximately 3 minutes), the reaction mixture was stirred for 10 minutes and quenched with water. The off-white amorphous precipitate was washed with water and methanol upon collection, 554 mg (87%), mp 174–176° C.; $^1$H NMR (CDCl$_3$): δ 8.39 (s, 1H), 4.16 (s, 3H), 4.14 (s, 3H), 4.04 (s, 3H), 2.60 (s, 3H); MS (APCI): m/z 308 (M+H). Anal. Calcd. for C$_{13}$H$_{13}$N$_3$O$_6$: C, 50.82; H, 4.26; N, 13.68. Found: C, 50.65; H, 4.20; N, 13.39.

2,3-Dimethoxy-6-methyl-7-nitro-quinoxaline-5-carboxylic Acid (12)

To a suspension of 2,3-dimethoxy-6-methyl-7-nitro-quinoxaline-5-carboxylic acid methyl ester (11) (1.61 g, 5.24 mmol) in THF 20 mL was added a solution of potassium hydroxide (85%) in 20 mL water (0.86 g, 13.09 mmol). After stirring at room temperature for 20 hours, all solid went into solution. The reaction was allowed to continue for an additional 7 hours and was then cooled to 0° (ice water bath). Acidification with aqueous 1.0 N hydrochloric acid produced a white, amorphous precipitate which was recrystallized from ethyl acetate to give 1.47 g (95%) product, mp 258–260° C.; $^1$H NMR (DMSO-d$_6$): δ 12.37 (br s, 1H), 8.09 (s, 1H), 3.93 (s, 3H), 3.89 (s, 3H), 2.34 (s, 3H); MS (APCI): m/z 294 (M+H). Anal. Calcd. for C$_{12}$H$_{11}$N$_3$O$_6$: C, 49.15; H, 3.78; N, 14.33. Found: C, 49.19; H, 3.53; N, 14.28.

2,3-Dimethoxy-6-methyl-7-nitro-quinoxaline-5-carbonyl Chloride (13)

A mixture of 2,3-dimethoxy-6-methyl-7-nitro-quinoxaline-5-carboxylic acid (12) (500 mg, 1.70 mmol) in thionyl chloride (twice distilled over triphenyl phosphite) (25 mL) was heated at reflux for 20 hours. The reaction mixture was concentrated to an off-white solid which was purified by elution through a flash column (4:1 hexanes:ethyl acetate), 510 mg (96%), mp 162–164° C.; $^1$H NMR (CDCl$_3$): δ 8.35 (s, 1H), 4.15 (s, 3H), 4.03 (s, 3H), 2.55 (s, 3H); MS: m/z 312 (M+H). Anal Calcd. for C$_{12}$H$_{11}$ClN$_3$O$_5$: C, 46.24; H, 3.23; N, 13.48. Found: C, 46.38; H, 3.32; N, 13.28.

[(2,3-Dimethoxy-6-methyl-7-nitro-quinoxaline-5-carbonyl)-amino]acetic Acid Tert-butyl Ester (14a) (General procedure for synthesis of compounds 14b–m)

To a mixture of glycine tert-butyl ester hydrochloride 104 mg (0.67 mmol) and triethylamine in 3 mL anhydrous tetrahydrofuran 0.26 mL (1.69 mmol) under an atmosphere of nitrogen was added dropwise a solution of 2,3-dimethoxy-6-methyl-7-nitro-quinoxaline-5-carbonyl chloride (13) 200 mg (0.64 mmol) in 7 mL anhydrous tetrahydrofuran at 0° C. After the addition was complete (approximately 5 minutes), the reaction mixture was stirred at room temperature for 24 hours, filtered, and concentrated. The residue was taken up in ethyl acetate and the organic solution was washed with water, saturated aqueous sodium chloride, dried over sodium sulfate, filtered and concentrated. The crude product was purified by elution through a flash column (silica gel 60, 230–400 mesh, 3:2 hexanes/ethyl acetate) to give a yellow oil which crystallized on standing, 200 mg (77%), mp 125–126° C.; $^1$H NMR (CDCl$_3$): δ 8.32 (s, 1H, 8-H), 6.32 (br s, 1H, amide NH), 4.14 (d, 2H, J=5.1 Hz), 4.09 (s, 3H), 3.99 (s, 3H), 2.54 (s, 3H), 1.47 (s, 9H, tert-butyl protons); MS (APCI): m/z 407 (M+H). Anal. Calcd. for C$_{18}$H$_{22}$N$_4$O$_7$: C, 53.20; H, 5.46; N, 13.79. Found: C, 53.24; H, 5.45; N, 13.55.

[(2.3-Dimethoxy-6-methyl-7-nitro-quinoxaline-5-carbonyl)-methylamino]-Acetic Acid, Tert-butyl Ester (14b)

Prepared from 2,3-dimethoxy-6-methyl-7-nitro-quinoxaline-5-carbonyl chloride (13) 200 mg (0.64 mmol) and sarcosine tert-butyl ester hydrochloride 122 mg (0.67 mmol). Reaction was continued for 24 hours, and the crude product was eluted through a flash column (4:1 hexanes:ethyl acetate), 200 mg (74%), mp 102–105° C.; $^1$H NMR (CDCl$_3$): δ 8.29 (s, 1H), 4.27 (br s, 2H), 4.02 (s, 3H), 3.96 (s, 3H), 3.35 (br s, 3H), 2.54 (s, 3H), 1.41 (s, 9H); MS (APCI): m/z 421 (M+H). Anal. Calcd. for C$_{19}$H$_{24}$N$_4$O$_7$: C, 54.28; H, 5.75; N, 13.33. Found: C, 54.51; H, 5.76; N, 13.35.

3-[(2,3-Dimethoxy-6-methyl-7-nitro-quinoxaline-5-carbonyl)-amino]-propionic Acid, Tert-butyl Ester (14c)

Prepared from 2,3-dimethoxy-6-methyl-7-nitro-quinoxaline-5-carbonyl chloride (13) 250 mg (0.80 mmol) and β-alanine tert-butyl ester hydrochloride 153 mg (0.80 mmol). Reaction was continued for 2.5 hours, and the crude product was eluted through a flash column (3:2 hexanes:ethyl acetate), 230 mg (68%), mp 140–142° C., R$_f$ 0.47 (1:1 hexanes:ethyl acetate); $^1$H NMR (CDCl$_3$): δ 8.31 (s, 1H), 6.37 (br s, 1H), 4.08 (s, 3H), 3.97 (s, 3H), 3.74 (q, 2H, methylene protons, J=6.1 Hz), 2.57 (t, 2H, J=6.3 Hz, J=6.1 Hz), 2.55 (s, 3H), 1.42 (s, 9H); MS (APCI): m/z 421 (M+H). Anal. Calcd. for C$_{19}$H$_{24}$N$_4$O$_7$: C, 54.28; H, 5.75; N, 13.33. Found: C, 54.25; H, 5.69; N, 13.00.

(S)-2-[(2,3-Dimethoxy-6-methyl-7-nitro-quinoxaline-5-carbonyl)-amino]-3-phenylpropionic Acid, Tert-butyl Ester (14d)

Prepared from 2,3-dimethoxy-6-methyl-7-nitro-quinoxaline-5-carbonyl chloride (13) 200 mg (0.64 mmol) and L-phenylalanine, tert-butyl ester hydrochloride 173 mg (0.67 mmol). Reaction was continued for 24 hours, and the crude product was eluted through a flash column (4:1 hexanes:ethyl acetate), 180 mg (57%), mp 86–88° C.; $^1$H NMR (CDCl$_3$): δ 8.32 (s, 1H), 7.22 (m, 5H), 6.39 (d, 1H, J=6.6 Hz), 4.88 (q, 1H, J=6.1, J=6.8 Hz), 4.07 (s, 3H), 4.00 (s, 3H), 3.23 (d, 2H, J=5.9 Hz), 2.56 (s, 3H), 1.37 (s, 9H); MS (APCI): m/z 497 (M+H). Anal. Calcd. for C$_{25}$H$_{28}$N$_4$O$_7$: C, 60.48; H, 5.68; N, 11.28. Found: C, 59.73; H, 5.53; N, 11.28.

2,3-Dimethoxy-6-methyl-7-nitro-quinoxaline-5-carboxylic Acid Dimethylamide (14e)

Prepared from 2,3-dimethoxy-6-methyl-7-nitro-quinoxaline-5-carbonyl chloride (13) 250 mg (0.80 mmol) and an excess of a solution of gaseous dimethylamine bubbled into anhydrous THF. Reaction was continued for 19 hours, and the crude product was eluted through a flash column (7:3 hexanes:ethyl acetate), 260 mg (100%), mp 138–141° C.; $^1$H NMR (CDCl$_3$): δ 8.29 (s, 1H, 8-H), 4.03 (s, 3H, OCH$_3$), 3.96 (s, 3H, OCH$_3$), 3.28 (s, 6H, N(CH$_3$)$_2$), 2.54 (s, 3H, 6-CH$_3$); MS (APCI): m/z 321 (M+H). Anal. Calcd. for C$_{14}$H$_{16}$N$_4$O$_5$: C, 52.50; H, 5.03; N, 17.49. Found: C, 52.54; H, 5.01;N, 17.30.

2,3-Dimethoxy-6-methyl-7-nitro-quinoxaline-5-carboxylic Acid Methylamide (14f)

Prepared from 2,3-dimethoxy-6-methyl-7-nitro-quinoxaline-5-carbonyl chloride (13) 250 mg (0.80 mmol) and an excess of a solution of gaseous monomethylamine bubbled into anhydrous THF. Reaction was continued for 17 hours, and the crude product was eluted through a flash column (11:9 hexanes:ethyl acetate), 190 mg (76%), mp 205–206° C.; $^1$H NMR (CDCl$_3$): δ 8.32 (s, 1H), 5.83 (br s, 1H), 4.07 (s, 3H), 3.98 (s, 3H), 3.07 (d, 3H, J=5.1 Hz), 2.56 (s, 3H); MS (APCI): m/z 307 (M+1). Anal. Calcd. for C$_{13}$H$_{14}$N$_4$O$_5$: C, 50.98; H, 4.61; N, 18.29. Found: C, 51.12; H, 4.72; N, 18.25.

2,3-Dimethoxy-6-methyl-7-nitro-quinoxaline-5-carboxylic Acid Benzylamide (14g)

Prepared from 2,3-dimethoxy-6-methyl-7-nitro-quinoxaline-5-carbonyl chloride (13) 250 mg (0.80 mmol) and benzylamine 90 μL (0.84 mmol). Reaction was continued for 24 hours, and the crude product was eluted through a flash column (7:3 hexanes:ethyl acetate), 260 mg (84%), mp 171–173° C.; $^1$H NMR (CCl$_3$): δ 8.32 (s, 1H), 7.32 (m, 5H), 6.12 (br s, 1H), 4.68 (d, 2H, J=5.6 Hz), 4.06 (s, 3H), 3.92 (s, 3H), 2.56 (s, 3H); MS (APCI): m/z 383 (M+1). Anal Calcd. for C$_{19}$H$_{18}$N$_4$O$_5$: C, 59.68; H, 4.74; N, 14.65. Found: C, 59.63; H, 4.94; N, 14.56.

2,3-Dimethoxy-6-methyl-7-nitro-quinoxaline-5-carboxylic acid, 4-methoxy-benzylamide (14h)

Prepared from 2,3-dimethoxy-6-methyl-7-nitro-quinoxaline-5-carbonyl chloride (13) 250 mg (0.80 mmol) and 4-methoxybenzylamine 0.11 mL (0.84 mmol). Reaction was continued for 16 hours, and the crude product was recrystallized from hexanes:ethyl acetate to give yellow needles, 156 mg (47%), mp 187–189° C.; $^1$H NMR (CDCl$_3$): δ 8.32 (s, 1H, 8-H), 7.28 (d, 2H, J=8.5 Hz), 6.85 (d, 2H, J=8.5 Hz), 6.07 (bs, 1H), 4.61 (d, 2H, J=5.6 Hz), 4.05 (s, 3H), 3.97 (s, 3H), 3.76 (s, 3H), 2.56 (s, 3H); MS (APCI): m/z 413 (M+1). Anal. Calcd. for C$_{20}$H$_{20}$N$_4$O$_6$: C, 58.25; H, 4.89; N, 13.59. Found: C, 58.55; H, 4.85; N, 13.47.

2.3-Dimethoxy-6-methyl-7-nitro-quinoxaline-5-carboxylic Acid Phenylamide (14i)

Prepared from 2,3-dimethoxy-6-methyl-7-nitro-quinoxaline-5-carbonyl chloride (13) 250 mg (0.80 mmol) and aniline 80 μL (0.84 mmol). Reaction was continued for 40 hours, and the crude product was eluted through a flash column (3:2 hexanes:ethyl acetate), 180 mg (62%), mp 238–240° C.; $^1$H NMR (CDCl$_3$): δ 8.34 (s, 1H), 7.81 (d, 2H, J=8.8 Hz), 7.69 (s, 1H), 7.35 (t, 2H, J=7.6, 8.5 Hz), 7.11 (t, 1H, J=6.3, J=7.3 Hz), 4.17 (s, 3H), 4.02 (s, 3H), 2.58 (s, 3H); (APCI): m/z 369 (M+H). Anal. Calcd. for C$_{18}$H$_{16}$N$_4$O$_5$: C, 58.69; H, 4.38; N, 15.21. Found: C, 58.62; H, 4.52; N, 15.06.

2,3-Dimethoxy-6-methyl-7-nitro-quinoxaline-5-carboxylic Acid (4-methoxyphenyl) Amide (14j)

Prepared from 2,3-dimethoxy-6-methyl-7-nitro-quinoxaline-5-carbonyl chloride (13) 250 mg (0.80 mmol) and 4-anisidine 207 mg (1.68 mmol). Reaction was continued for 24 hours, and the crude product was eluted through a flash column (3:2 hexanes:ethyl acetate), 210 mg (66%), mp 206–208° C.; $^1$H NMR (CDCl$_3$): δ 8.33 (s, 1H), 7.71 (d, 2H, J=9.0 Hz), 7.60 (s, 1H), 6.88 (d, 2H, J=8.8 Hz), 4.16 (s, 3H), 4.00 (s, 3H), 3.79 (s, 3H), 2.57 (s, 3H); MS (APCI): m/z 399 (M+H). Anal. Calcd. for C$_{19}$H$_{18}$N$_4$O$_6$: C, 57.29; H, 4.55; N, 14.06. Found: C, 57.23; H, 4.73; N, 14.01.

(2,3-Dimethoxy-6-methyl-7-nitro-quinoxalin-5-yl)-piperazin-1-yl Methanone (14k)

Prepared from 2,3-dimethoxy-6-methyl-7-nitro-quinoxaline-5-carbonyl chloride (13) 250 mg (0.80 mmol) and piperazine 138 mg (1.60 mmol). Reaction was continued for 2 hours, and the crude product was eluted through a flash column (8% methanol in chloroform): 250 mg (86%), mp 150–152° C.; $^1$H NMR (CDCl$_3$): δ 8.30 (s, 1H), 4.05 (s, 3H), 3.96 (s, 3H), 3.81 (t, 4H, J=4.9, 5.1 Hz), 2.96 (t, 4H, J=5.1, 4.9 Hz), 2.54 (s, 3H), 1.84 (br s, 1H); MS (APCI): m/z 362 (M+H). Anal. Calcd. for $C_{16}H_{19}N_5O_5$: C, 53.18; H, 5.30; N, 19.38. Found: C, 53.08; H, 5.22; N, 18.82.

[1,4]Diazepan- 1-yl-(2,3-dimethoxy-6-methyl-7-nitro-quinoxalin-5-yl)Methanone (14l)

Prepared from 2,3-dimethoxy-6-methyl-7-nitro-quinoxaline-5-carbonyl chloride (13) 250 mg (0.80 mmol) and homopiperazine 160 mg (1.60 mmol). Reaction was continued for 30 hours, and the crude product was eluted through a flash column (8% methanol in chloroform), 260 mg (87%), mp 141–143° C.; $^1$H NMR (CDCl$_3$): δ 8.29 (s, 1H), 4.03 (s, 3H), 3.93 (br s, 7H), 3.02 (br s, 2H), 2.82 (t, 2H, J=5.4, J=5.6 Hz), 2.54 (s, 3H), 1.88 (t, 2H, J=5.6, 5.4 Hz), 1.79 (bs, 1H); MS (APCI): m/z 376 (M+H). Anal. Calcd. for $C_{17}H_{21}N_5O_5$: C, 54.39; H, 5.64; N, 18.66. Found: C, 54.07; H, 5.57; N, 18.24.

2.3-Dimethoxy-6-methyl-7-nitro-quinoxaline-5-carboxylic Acid, p-Tolylamide (14m)

Prepared from 2,3-dimethoxy-6-methyl-7-nitro-quinoxaline-5-carbonyl chloride (13) 250 mg (0.80 mmol) and p-toluidine 180 mg (1.68 mmol). Reaction was carried out in refluxing tetrahydrofuran for 50 hours, and the crude product was eluted through a flash column (7:3 hexanes-:ethyl acetate), 200 mg (65%), mp 214–215° C.; $^1$H NMR (CDCl$_3$): δ 8.33 (s, 1H), 7.69 (d, 2H, J=8.3 Hz), 7.65 (s, 1H), 7.15 (d, 2H, J=8.3 Hz), 4.17 (s, 3H), 4.03 (s, 3H), 2.58 (s, 3H), 2.32 (s, 3H); MS (APCI): m/z 383 (M+H). Anal Calcd. for $C_{19}H_{18}N_4O_5$: C, 59.68; H, 4.74; N, 14.65. Found: C, 59.97; H, 4.68; N, 14.71.

[(6-Methyl-7-Nitro-2.3-dioxo- 1,2,3,4-tetrahydro-quinoxaline-5-carbonyl)-amino]-acetic Acid (15)

To a stirred mixture of [(2,3-Dimethoxy-6-methyl-7-nitro-quinoxaline-5-carbonyl)-amino] acetic acid tert-butyl ester (14a) 150 mg (0.37 mmol) and sodium iodide 555 mg (3.7 mmol) in 25 mL acetonitrile is added dropwise chlorotrimethylsilane 0.46 mL (3.7 mmol). After addition was complete, the reaction mixture was refluxed under an atmosphere of nitrogen for 72 hours. The reaction mixture was quenched by pouring into 100 mL water, and the aqueous mixture was concentrated to 10 mL. The residue was mixed with ethyl acetate, and after stirring for 30 minutes, the product precipitated, 35 mg (29%), mp 250° C. (dec.); $^1$H NMR (DMSO-d$_6$): δ 12.55 (br s, 1H), 8.40 (t, 1H, J=6.3 Hz), 7.84 (s, 1H), 4.07 (d, 2H, J=6.3 Hz), 2.43 (s, 3H); MS (APCI): m/z 323 (M+H). Anal. Calcd. for $C_{12}H_{10}N_4O_7$: C, 44.73; H, 3.13; N, 17.39. Found: C, 41.38; H, 3.12; N, 15.79.

EXAMPLE 2

Scheme II procedure follows as indicated below.

6-Methyl-1-7-nitro-quinoxaline-2,3-dione-5-hydrazide (4)

From Quinoxaline-2,3-dione-5-methyl ester (A) (Compound 8 of Scheme I)

A solution of A (1.00 g, 3.6 mmol) in anhydrous hydrazine (10 mL) was stirred at room temperature under nitrogen for 24 hours. The solvent was removed under reduced pressure, and the residue was taken up in boiling water and filtered hot. Upon cooling the hydrazide precipitated as a yellow, crystalline solid (806 mg, 80%). MS (Cl) m/z=280 (M+1).

5-(5-Amino-[1,3,4]oxadiazol-2-yl)-6-methyl-7-nitro-14-dihydro-quinoxaline-2.3-dione (6)

A mixture of compound 4 (300 mg, 1.08 mmol) and KHCO$_3$ (124 mg, 1.24 mmol) in water (20 mL) was heated to 70° C., at which point all solid went into solution. A solution of cyanogen bromide (126 mg, 1.19 mmol) in water (3 mL) was added dropwise. Approximately 30 seconds after addition was complete, the product began to precipitate. The reaction mixture was kept at 70° C. for 1 hour and upon cooling, compound 6 was collected and washed with both water and acetone (84 mg, 26%). MS (Cl) m/z=305 (M+1).

6-Methyl-7-nitro-5-(5-oxo-4,5-dihydro-[ 1,3,4]oxadiazol-2-yl)- 1,4-dihydro-quinoxaline-2,3-dione (5)

A suspension of compound 4 (150 mg, 0.54 mmol) in anhydrous THF (10 mL) under nitrogen was treated dropwise with a 20% phosgene solution in toluene (10 mL). After stirring for 23 hours at room temperature, the precipitate was collected and washed with methanol to give an off-white solid (82 mg, 50%). MS (Cl) m/z=306 (M+1).

The compounds of the invention exhibit valuable biological properties because of their strong excitatory amino acid (EAA) antagonizing properties at one of several binding sites on glutamate receptors: the AMPA ((RS)-amino-3-hydroxy-5-methyl-4-isoxazole)-propionic acid (or kainic acid) binding site on AMPA (non-NMDA) receptors or the glycine site of NMDA receptors.

The compounds of the present invention exhibit binding affinity for the AMPA receptors measured as described in Honore T., et al., *Neuroscience Letters*, 1985;54:27–32. Preferred compounds demonstrate IC$_{50}$ values: <100 μM in this assay. The compounds of the present invention exhibit binding affinity for the kainate site (non-NMDA receptor) measured as described in London E. D. and Coyle J., *Mol. Pharmacol.*, 1979;15:492. The compounds of the present invention exhibit binding affinity for the glycine site of the NMDA receptor measured as described in Jones S. M., et al., *Pharmacol. Methods*, 1989;21:161. To measure functional AMPA antagonist activity, the effects of the agent on AMPA-induced neuronal damage in primary cortical neuronal cultures was examined using techniques similar to those outlined by Koh J-Y., et al., *J. Neurosci.*, 1990;10:693. In addition, the neuronal damage produced by long-term exposure to 100 μM AMPA may be measured by the release of the cytosolic enzyme lactate dehydrogenase (LDH).

Selected compounds of the present invention were tested by one or more of the above-described assays. The data obtained in the assays is set forth in Table 1 below. The IC$_{50}$ values set forth in Table 1 is a measure of the concentration (μM) of the test substance which inhibits 50% of an induced release from the tested receptors.

TABLE OF BIOLOGICAL ACTIVITY 1. 5-(5-Amino-[1,3,4]oxadiazo-1-2yl)-6-methyl-7-nitro-1,4-dihydro-quinoxaline-2,3-dione

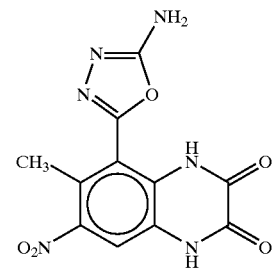

2. 6-Methyl-7-nitro-5-(-oxo-4,5-dihydro-[1,3,4]oxadiazo-1-2-yl-1,4-dihydro-quinoxaline-2,3-dione

TABLE OF BIOLOGICAL ACTIVITY

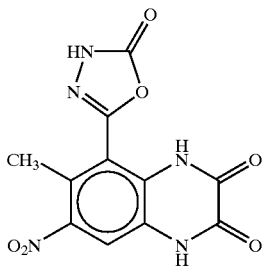

| Example | IC$_{50}$ AMPA | IC$_{50}$ GLY |
|---------|----------------|---------------|
| 1 | 0.4 | 0.06 |
| 2 | 0.5 | — |

While the forms of the invention herein disclosed constitute presently preferred embodiments, many others are possible. It is not intended herein to mention all of the possible equivalent forms or ramifications of the invention. It is understood that the terms used herein are merely descriptive rather than limiting, and that various changes may be made without departing from the spirit or scope of the invention.

What is claimed is:

1. A process for the preparation of a compound of formula

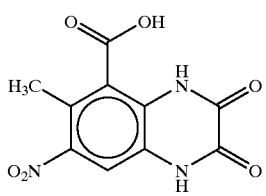

comprising a) reacting a compound of formula,

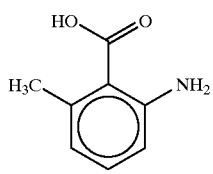

with phosgene in the presence of an inorganic base;
b) brominating the product of step a) above in a solution of AcOH/TFA;
c) nitrating the product of step b) above with KNO$_3$/H$_2$SO$_4$;
d) treating the product of step c) above with an alcohol;
e) reducing catalytically the product of step d) above with Raney Nickel and with hydrogen donating solvents under a hydrogen atmosphere in the presence of a base;
f) treating the product of step e) above with an oxalic acid derivative in a polar solvent or an ethereal solvent;
g) nitrating the product of step f) above with a nitrating mixture and isolating the product; and
h) hydrolyzing the product of step g) above in the presence of a base in a water soluble solvent.

2. A process for preparing a compound of formula

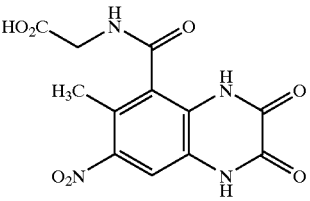

comprising a) treating a compound of formula

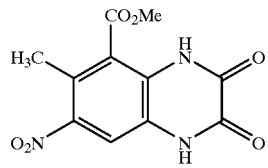

in DMF with phosgene solution in toluene and precipitating to produce a dichloro compound of formula

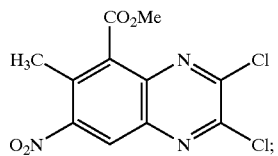

b) adding the product of step a) above to a solution of sodium metal in anhydrous methanol under an atmosphere of nitrogen to produce a dimethoxy compound;
c) adding a solution of potassium hydroxide in water to the product of step b) above and stirring until all the solid is in solution, acidifying to produce a precipitate;
d) refluxing a mixture of the product of step c) above in thionylchloride and concentrating the reaction mixture;
e) adding the product of step d) above dropwise to a mixture of glycine tert-butyl ester hydrochloride and triethylamine in tetrahydrofuran under an atmosphere of nitrogen; and
f) adding chlorotrimethylsilane dropwise to a stirred mixture of the product of step e) above and sodium iodide in acetonitrile and refluxing.

* * * * *